United States Patent
Mignon et al.

(10) Patent No.: US 10,881,594 B2
(45) Date of Patent: Jan. 5, 2021

(54) ANHYDROUS SOLID COMPOSITION FOR DYEING KERATIN FIBRES COMPRISING A METABISULFITE

(71) Applicant: L'OREAL, Paris (FR)

(72) Inventors: Marie Mignon, Saint Ouen (FR); Chrystel Pourille, Saint Ouen (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/471,636

(22) PCT Filed: Dec. 19, 2017

(86) PCT No.: PCT/EP2017/083441
§ 371 (c)(1),
(2) Date: Jun. 20, 2019

(87) PCT Pub. No.: WO2018/114885
PCT Pub. Date: Jun. 28, 2018

(65) Prior Publication Data
US 2020/0085709 A1 Mar. 19, 2020

(30) Foreign Application Priority Data
Dec. 20, 2016 (FR) ..................... 16 62927

(51) Int. Cl.
A61Q 5/10 (2006.01)
A61K 8/23 (2006.01)
(Continued)

(52) U.S. Cl.
CPC .................. A61K 8/23 (2013.01); A45D 7/00 (2013.01); A45D 33/005 (2013.01); A45D 37/00 (2013.01);
(Continued)

(58) Field of Classification Search
CPC .. A61Q 5/10; A61K 8/415; A61K 2800/4324; A61K 2800/31; A61K 8/23; A45D 33/005; A45D 2007/001
(Continued)

(56) References Cited

U.S. PATENT DOCUMENTS

2004/0216242 A1 11/2004 Kravtchenko et al.
2005/0015897 A1 1/2005 Audousset
(Continued)

FOREIGN PATENT DOCUMENTS

FR 2 917 967 A1 1/2009
FR 2 917 973 A1 1/2009
FR 3 015 232 A1 6/2015

OTHER PUBLICATIONS

Perfumaria Marcia-Aney, Colourant Powder—MINTEL Record ID 1148517, Jul. 2009, XP-002769576.

Primary Examiner — Eisa B Elhilo
(74) Attorney, Agent, or Firm — Polsinelli PC

(57) ABSTRACT

The present invention relates to an anhydrous solid composition for dyeing keratin fibres, in particular human keratin fibres such as the hair, comprising one or more metabisulfites. The present invention also relates to a packaging article containing said composition. The present invention also relates to processes for dyeing keratin fibres using said composition or said packaging article. Finally, the present invention also relates to the use of said composition or of said packaging article for dyeing keratin fibres, and in particular human keratin fibres such as the hair.

20 Claims, 2 Drawing Sheets

(51) Int. Cl.
*A45D 7/00* (2006.01)
*A45D 33/00* (2006.01)
*A45D 37/00* (2006.01)
*A61K 8/11* (2006.01)
*A61K 8/41* (2006.01)
*A61K 8/46* (2006.01)

(52) U.S. Cl.
CPC ............... *A61K 8/11* (2013.01); *A61K 8/415* (2013.01); *A61K 8/463* (2013.01); *A61Q 5/10* (2013.01); *A45D 2007/001* (2013.01); *A61K 2800/4324* (2013.01); *A61K 2800/56* (2013.01)

(58) Field of Classification Search
USPC ............................................................ 8/524
See application file for complete search history.

(56) References Cited

U.S. PATENT DOCUMENTS

2010/0186177 A1* 7/2010 Hercouet ................ A61K 8/31
8/408
2010/0199441 A1* 8/2010 Hercouet ................ A61K 8/41
8/407
2013/0263390 A1 10/2013 Fadli et al.

* cited by examiner

ANHYDROUS SOLID COMPOSITION FOR DYEING KERATIN FIBRES COMPRISING A METABISULFITE

CROSS REFERENCE TO RELATED APPLICATIONS

This application is a National Phase filing under 35 U.S.C. § 371 of PCT/EP2017/083441 filed on Dec. 19, 2017; which application in turn claims priority to Application No. 1662927 filed in France on Dec. 20, 2016. The entire contents of each application are hereby incorporated by reference.

The present invention relates to an anhydrous solid composition for the oxidation dyeing of keratin fibres, in particular human keratin fibres such as the hair, comprising one or more metabisulfites.

The present invention also relates to a packaging article containing said composition.

The present invention also relates to processes for dyeing keratin fibres using said composition or said packaging article.

Finally, the present invention also relates to the use of said composition or of said packaging article for dyeing keratin fibres, and in particular human keratin fibres such as the hair.

For a long time, hair dyeing, and in particular the masking of grey hair, has been desired by numerous individuals.

It is known practice to dye keratin fibres, in particular human keratin fibres such as the hair, to obtain "permanent" colourations with dyeing compositions containing oxidation dye precursors, which are generally known as oxidation bases, such as ortho- or para-phenylenediamines, ortho- or para-aminophenols, or heterocyclic compounds such as pyrazoles, pyrazolinones or pyrazolo-pyridines. These oxidation bases are colourless or weakly coloured compounds, which, when combined with oxidizing products, may give rise to coloured compounds via a process of oxidative condensation.

It is also possible to vary the shades obtained with these oxidation bases by combining them with couplers or colour modifiers. The variety of molecules used as oxidation bases and couplers allows a wide range of colours to be obtained on the keratin fibres.

The oxidation dyeing process thus consists in applying to keratin fibres a dyeing composition comprising oxidation bases or a mixture of oxidation bases and couplers with hydrogen peroxide ($H_2O_2$ or aqueous hydrogen peroxide solution), as oxidizing agent, in leaving it to diffuse, and then in rinsing the fibres thus treated.

The colourings resulting therefrom have the advantage of being permanent, strong and resistant to external agents, in particular to light, bad weather, washing, perspiration and rubbing.

Although dyeing compositions can be in various galenic forms, such as powders, granules, pastes or creams, they are generally packaged in liquid form. However, solid dyeing compositions bring many advantages compared with liquid dyeing compositions. The process for producing them does not require water, thereby making it possible to adopt a more eco-friendly behaviour. It can also be miniaturized.

However, the solid dyeing compositions currently on the market exhibit, after several weeks of storage, problems of stability which result in a premature oxidation of the dyes and a decrease in dyeing performance qualities once the composition is used. Moreover, once oxidized, the composition has a tendency to turn dark, which is not popular with consumers.

In order to compensate for this oxidation, many dyeing compositions in solid form comprise amounts of oxidation dyes that are higher than the amounts of dyes contained in liquid compositions. Solving this oxidation problem by increasing the amounts of base of the dyes in the composition is not satisfactory. Indeed, this solution is not economically advantageous. Moreover, the handling and/or application of large amounts of dyes on the hair can pose a problem due to their toxicological profile.

At the current time, there is no dyeing composition in solid form that is satisfactory in terms of stability and that has a degree of dyeing quality similar to liquid dyeing compositions.

Finally, the formulations in solid form make it possible to use raw materials that are unstable or have low stability in liquid formulation.

Thus, there is a real need to provide solid dyeing compositions which do not have the abovementioned drawbacks, i.e. which remain stable over time and which retain their dyeing properties.

These compositions must also lead to chromatic, powerful, intense and sparingly selective colourings, that is to say colourings that are uniform along the length of the keratin fibre.

The applicant has discovered, surprisingly, that an anhydrous solid dyeing composition comprising one or more oxidation bases and one or more metabisulfites makes it possible to achieve the objectives set out above, in particular to obtain a solid dyeing composition that is stable over time, and the dyeing properties of which are maintained even after several months of storage.

A subject of the present invention is in particular an anhydrous solid composition for dyeing keratin fibres, in particular human keratin fibres such as the hair, comprising:
  one or more oxidation bases,
  one or more metabisulfites, and
optionally one or more oxidation couplers.

The present invention also relates to a ready-to-use composition comprising an anhydrous solid dyeing composition, as defined above, one or more chemical oxidizing agents, and optionally a cosmetically acceptable medium.

The presence of metabisulfite(s) makes it possible to limit the oxidation of the composition, thus improving its stability over time. The composition thus stabilized retains its dyeing properties. In other words, the metabisulfite makes it possible to maintain the dyeing properties of the composition over time without recourse to an increase in the dye content.

Thus, the composition according to the invention makes it possible to produce chromatic, powerful, intense and sparingly selective colourings, even after several months of storage.

A subject of the present invention is also a packaging article comprising:
i) an envelope defining at least one cavity, the envelope comprising water-soluble and/or liposoluble fibres, preferably water-soluble fibres; and
ii) an anhydrous solid dyeing composition as defined previously;
it being understood that the anhydrous solid dyeing composition is in one of the cavities defined by the envelope i).

The present invention also relates to a process for dyeing keratin fibres, in particular human keratin fibres such as the hair, comprising the following successive steps:
  applying to said keratin fibres a ready-to-use composition as defined previously,
  leaving the ready-to-use composition on said keratin fibres, rinsing said keratin fibres, and optionally shampooing said keratin fibres, rinsing them and drying them.

A subject of the present invention is also a process for dyeing keratin fibres, in particular human keratin fibres such as the hair, comprising the following successive steps:

mixing a packaging article, as defined previously, with a composition capable of dissolving the envelope of said packaging article, and optionally one or more chemical oxidizing agents, applying the resulting composition to said keratin fibres, leaving said resulting composition on said keratin fibres, rinsing said keratin fibres, and optionally shampooing said keratin fibres, rinsing them and drying them.

The present invention also relates to the use of a ready-to-use composition, as defined previously, for dyeing keratin fibres, and in particular human keratin fibres such as the hair.

The present invention also relates to the use of a packaging article, as defined previously, for dyeing keratin fibres, and in particular human keratin fibres such as the hair.

Other subjects, characteristics, aspects and advantages of the invention will emerge even more clearly on reading the description and the examples that follow.

BRIEF DESCRIPTION OF DRAWINGS

FIG. 1a) is a cross section of a particular embodiment of the packaging article.

Figure 1A:
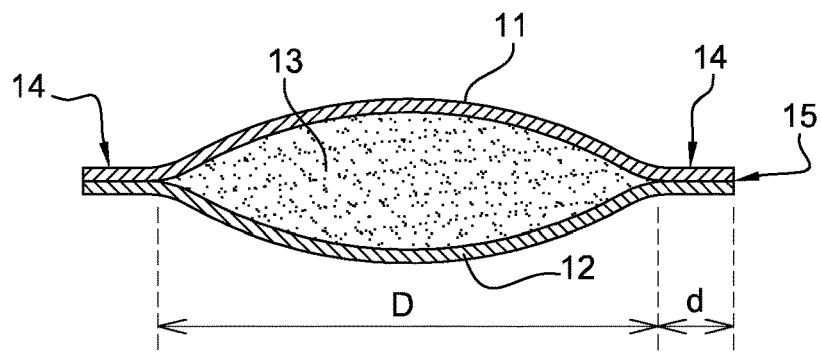
FIGS. 1a)-1e) illustrate an embodiment of a packaging article that can contain the composition according to the invention.

In the text hereinbelow, and unless otherwise indicated, the limits of a range of values are included within that range, especially in the expressions "between" and "ranging from . . . to . . . ".

Moreover, the expressions "at least one" and "at least" used in the present description are equivalent to the expressions "one or more" and "greater than or equal to", respectively.

The term "keratin materials" preferably denotes human keratin materials, such as the skin, the scalp and keratin fibres that are human, and more preferentially the hair.

The term "anhydrous composition" is intended to mean a composition comprising a water content of less than 3% by weight, preferably less than 1% by weight, relative to the weight of the composition. Preferably, this water content is less than 0.5% by weight relative to the weight of the composition. More particularly, the water content ranges from 0 to 1% by weight and preferably from 0 to 0.5% by weight relative to the total weight of the composition. Finally, more particularly, it does not comprise water.

The term "solid composition" is intended to mean a composition that can be in powder, paste or particle form (for example spherical particles such as small balls).

The term "powder" is intended to mean a composition in pulverulent form, which is preferably essentially free of dust (or fine particles). In other words, the particle size distribution of the particles is such that the weight ratio of particles less than or equal to 100 micrometres in size (fines content) and preferably less than or equal to 65 micrometres in size (fines content) is advantageously less than or equal to 5%, preferably less than 2% and more particularly less than 1% (particle size evaluated using a Retsch AS 200 Digit particle size analyser; oscillation height: 1.25 mm/screening time: 5 minutes). Advantageously, the particle size is between 100 µm and 3 mm and more particularly between 65 µm and 2 mm.

The term "paste" is intended to mean a composition with a viscosity of greater than 5 poises and preferably greater than 10 poises, measured at 25° C. and at a shear rate of 1 $s^{-1}$; this viscosity may be determined using a cone-plate rheometer.

The term "particles" is intended to mean small fractionated objects formed from solid particles aggregated together, of variable shapes and sizes. They may be regular or irregular in shape. They may in particular have a spherical shape (such as granules, granular material, balls), a square shape, a rectangular shape, or an elongated shape such as rods. Spherical particles are quite particularly preferred.

The size of the particles can be, in the largest dimension thereof, between 0.01 and 5 mm, preferably between 0.1 and 2.5 mm, and better still between 0.5 and 2 mm.

The anhydrous solid composition according to the invention can be in the form of a compressed solid composition, in particular compressed using a manual or mechanical press.

Anhydrous Solid Dyeing Composition

Oxidation Bases

The anhydrous solid dyeing composition according to the present invention comprises one or more oxidation bases. Preferably, the oxidation bases are chosen especially from heterocyclic bases and benzene-based bases, the addition salts thereof, the solvates thereof, and mixtures thereof.

The oxidation bases that may be used in the composition of the invention are chosen especially from para-phenylenediamines, bis(phenyl)alkylenediamines, para-aminophenols, ortho-aminophenols and heterocyclic bases, the addition salts thereof, the solvates thereof, and mixtures thereof.

Among the para-phenylenediamines that may be mentioned are, for example, para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis((3-hydroxyethyl)amino-2-methylaniline, 4-N,N-bis((3-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N-((3-hydroxypropyl)-para-phenylenediamine, 2-hydroxymethyl-para-phenylenediamine, N,N-dimethyl-3-methyl-para-phenylenediamine, N-ethyl-N-((3-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-((3-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the corresponding addition salts with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis((3-hydroxyethyl)-para-phenylenediamine, 2-chloro-para-phenylenediamine and 2-β-acetylamino ethyloxy-para-phenylenediamine, and the corresponding addition salts with an acid, are particularly preferred.

Among the bis(phenyl)alkylenediamines that may be mentioned, for example, are N,N'-bis((3-hydroxyethyl)-N,N'-bis(4'-aminophenyl)-1,3-diaminopropanol, N,N'-bis((3-hydroxyethyl)-N,N'-bis(4'-aminophenyl)ethylenediamine, N,N'-bis(4-aminophenyl)tetramethylenediamine, N,N'-bis((3-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylene diamine and 1,8-bis(2,5-diaminophenoxy)-3,6-dioxaoctane, and the corresponding addition salts.

Among the para-aminophenols that are mentioned are, for example, para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-((3-hydroxyethylaminomethyl)phenol and 4-amino-2-fluorophenol, and the corresponding addition salts with an acid.

Among the ortho-aminophenols that may be mentioned, for example, are 2-aminophenol, 2-amino-5-methylphenol, 2-amino-6-methylphenol and 5-acetamido-2-aminophenol, and the corresponding addition salts.

Among the heterocyclic bases that may be mentioned, for example, are pyridine, pyrimidine and pyrazole derivatives.

Among the pyridine derivatives that may be mentioned are the compounds described, for example, in patents GB 1 026 978 and GB 1 153 196, for example 2,5-diaminopyridine, 2-(4-methoxyphenyl)amino-3-aminopyridine and 3,4-diaminopyridine, and the corresponding addition salts.

Other pyridine oxidation bases that are useful in the present invention are the 3-aminopyrazolo[1,5-a]pyridine oxidation bases or the corresponding addition salts described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-β-hydroxyethoxy-3-aminopyrazolo[1,5-a]pyridine and 2-(4-dimethylpiperazinium-1-yl)-3-aminopyrazolo[1,5-a]pyridine, and the corresponding addition salts.

More particularly, the oxidation bases that are useful in the present invention are chosen from 3-aminopyrazolo[1,5-a]pyridines and are preferably substituted on carbon atom 2 with:

a) a (di)($C_1$-$C_6$)(alkyl)amino group, said alkyl group possibly being substituted with at least one hydroxyl, amino or imidazolium group;

b) an optionally cationic 5- to 7-membered heterocycloalkyl group comprising from 1 to 3 heteroatoms, optionally substituted with one or more ($C_1$-$C_6$)alkyl groups such as a di($C_1$-$C_4$)alkylpiperazinium group; or c) a ($C_1$-$C_6$)alkoxy group optionally substituted with one or more hydroxyl groups, such as a β-hydroxyalkoxy group, and the corresponding addition salts.

Among the 3-aminopyrazolo[1,5-a]pyridine bases, it will in particular be preferred to use 2[(3-aminopyrazolo[1,5-a]pyridin-2-yl)oxy]ethanol, and/or 4-(3-aminopyrazolo[1,5-a]pyridin-2-yl)-1,1-dimethylpiperazin-1-ium chloride and/or the corresponding addition salts or solvates thereof.

Among the pyrimidine derivatives that may be mentioned are the compounds described, for example, in patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazole derivatives that may be mentioned are the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-((3-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-((3-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the corresponding addition salts. Use may also be made of 4,5-diamino-1-((3-methoxyethyl)pyrazole.

A 4,5-diaminopyrazole will preferably be used and even more preferentially 4,5-diamino-1-((3-hydroxyethyl)pyrazole and/or a corresponding salt.

The pyrazole derivatives that may also be mentioned include diamino-N,N-dihydropyrazolopyrazolones and in particular those described in patent application FR-A-2 886 136, such as the following compounds and the corresponding addition salts: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-bis(2- hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one and 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a corresponding salt.

Use will preferably be made of 4,5-diamino-1-((3-hydroxyethyl)pyrazole and/or 2,3-diamino-6,7-dihydro-1H,5H-pyrazolo[1,2-a]pyrazol-1-one and/or 2[(3-aminopyrazolo[1,5-a]pyridin-2-yl)oxy]ethanol and/or 4-(3-aminopyrazolo[1,5-a]pyridin-2-yl)-1,1-dimethylpiperazin-1-ium chloride and/or the corresponding salts or solvates thereof as heterocyclic bases.

In general, the addition salts of oxidation bases that may be used in the composition according to the invention are chosen in particular from the addition salts with an acid such as the hydrochlorides, hydrobromides, sulfates, citrates, succinates, tartrates, lactates, tosylates, benzenesulfonates, phosphates and acetates.

Moreover, the solvates of the oxidation bases more particularly represent the hydrates of said bases and/or the combination of said bases with a linear or branched $C_1$ to $C_4$ alcohol such as methanol, ethanol, isopropanol or n-propanol. Preferably, the solvates are hydrates.

Preferably, the oxidation base(s) are chosen from para-phenylenediamines, bis(phenyl)alkylenediamines, para-aminophenols, bis-para-aminophenols, ortho-aminophenols and heterocyclic bases, the addition salts thereof, the solvates thereof, and mixtures thereof.

More preferentially, the oxidation base(s) are chosen from para-phenylenediamines, para-aminophenols, the addition salts thereof, the solvates thereof, and mixtures thereof, and preferably from toluene-2,5-diamine, 1-hydroxy-4-aminobenzene, the addition salts thereof, the solvates thereof, and mixtures thereof.

The total amount of oxidation base(s) present in the anhydrous solid dyeing composition according to the invention preferably ranges from 0.1% to 45% by weight, more preferentially from 0.5% 40% by weight, better still from 1% to 35% by weight and even better still from 5% to 35% by weight, relative to the total weight of the anhydrous solid dyeing composition.

Metabisulfites

The anhydrous solid dyeing composition according to the present invention also comprises one or more metabisulfites.

The metabisulfite(s) according to the invention can preferably be chosen from alkali metal or alkaline-earth metal metabisulfites and mixtures thereof, more preferentially from alkali metal metabisulfites and mixtures thereof, and better still from sodium or potassium metabisulfites and mixtures thereof.

Particularly preferably, the metabisulfite is sodium metabisulfite.

The total amount of metabisulfite(s) present in the anhydrous solid dyeing composition according to the invention preferably ranges from 0.1% to 30% by weight, relative to the total weight of the anhydrous solid dyeing composition.

More particularly, the total amount of metabisulfite(s) ranges from 0.2% to 20% by weight, more preferentially from 1% to 20% by weight and better still from 3% to 10% by weight, relative to the total weight of the anhydrous solid dyeing composition.

More particularly, when the metabisulfite is sodium metabisulfite, the total amount of sodium metabisulfite present in the anhydrous solid dyeing composition according to the invention preferably ranges from 0.1% to 30% by weight, relative to the total weight of the anhydrous solid dyeing composition.

More preferentially when the metabisulfite is sodium metabisulfite, the total amount of sodium metabisulfite present in the anhydrous solid dyeing composition according to the invention ranges from 0.2% to 20% by weight, better still from 1% to 20% by weight and still from 3% to 10% by weight, relative to the total weight of the anhydrous solid dyeing composition.

Oxidation Couplers

The anhydrous solid dyeing composition according to the present invention can optionally also comprise one or more oxidation couplers conventionally used for dyeing keratin fibres.

Among these oxidation couplers, mention may be made in particular of meta-phenylenediamines, meta-aminophenols, meta-diphenols, naphthalene-based couplers and heterocyclic couplers, the addition salts thereof, the solvates thereof, and mixtures thereof.

Examples that may be mentioned include 2-methyl-5-hydroxyethylaminophenol, 2,4-diaminophenoxyethanol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-((3-hydroxyethylamino)-1-methoxybenzene, 1,3-diaminobenzene, 1,3-bis(2,4-diaminophenoxy)propane, 3-ureido aniline, 3-ureido-1-dimethylamino benzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazole-5-one, 1-phenyl-3-methylpyrazole-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, 2-methyl-5-aminophenol, 5-N-((3-hydroxyethyl)amino-2-methylphenol, 3-aminophenol and 3-amino-2-chloro-6-methylphenol, the corresponding addition salts with an acid and the corresponding mixtures.

Preferably, the oxidation coupler(s) are chosen from meta-phenylenediamines, meta-aminophenols, the addition salts thereof, the solvates thereof, and mixtures thereof, and preferably from 2-methyl-5-hydroxyethylaminophenol, 2,4-diaminophenoxyethanol, the addition salts thereof, the solvates thereof, and mixtures thereof.

The addition salts of the oxidation couplers optionally present in the composition according to the invention are chosen especially from the addition salts with an acid, such as the hydrochlorides, hydrobromides, sulfates, citrates, succinates, tartrates, lactates, tosylates, benzenesulfonates, phosphates and acetates, and the addition salts with a base such as sodium hydroxide, potassium hydroxide, ammonia, amines or alkanolamines.

Moreover, the solvates of the oxidation couplers more particularly represent the hydrates of said couplers and/or the combination of said couplers with a linear or branched $C_1$ to $C_4$ alcohol such as methanol, ethanol, isopropanol or n-propanol. Preferably, the solvates are hydrates.

The total amount of oxidation coupler(s), when they are present in the anhydrous solid dyeing composition according to the invention, preferably ranges from 0.1% to 45% by weight, more preferentially from 0.5% to 40% by weight, better still from 1% to 35% by weight and even better still from 5% to 35% by weight, relative to the total weight of the anhydrous solid dyeing composition.

Surfactants

The anhydrous solid dyeing composition according to the present invention can optionally also comprise one or more surfactants, preferably chosen from anionic surfactants, amphoteric or zwitterionic surfactants, non-ionic surfactants, cationic surfactants and mixtures thereof.

For the purposes of the present invention, the term "surfactant" is intended to mean an agent comprising at least one hydrophilic group and at least one lipophilic group in its structure, and which is preferably capable of reducing the surface tension of water, and comprising in its structure, as optional repeating units, only alkylene oxide units and/or sugar units and/or siloxane units. Preferably, the lipophilic group is a fatty chain comprising from 8 to 30 carbon atoms.

Preferably, the anhydrous solid dyeing composition according to the present invention comprises one or more surfactants chosen from anionic surfactants.

The term "anionic surfactant" is intended to mean a surfactant comprising, as ionic or ionizable groups, only anionic groups. These anionic groups are preferably chosen from the groups C(O)OH, C(O)O—, —SO$_3$H, —S(O)$_2$O$^-$, —OS(O)$_2$OH, —OS(O)$_2$O$^-$, —P(O)OH$_2$, —P(O)$_2$O$^-$, —P(O)O$_2^-$, —P(OH)$_2$, =P(O)OH, —P(OH)O$^-$, =P(O)O$^-$, =POH and =PO$^-$, the anionic parts comprising a cationic counterion such as those derived from an alkali metal, an alkaline-earth metal, an amine or an ammonium.

As examples of anionic surfactants that may be used in the composition according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulfosuccinamates, acylisethionates and N-acyltaurates, polyglycoside polycarboxylic acid and alkyl monoester salts, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds comprising from 6 to 24 carbon atoms and the aryl group denoting a phenyl group.

These compounds may be oxyethylenated and then preferably comprise from 1 to 50 ethylene oxide units.

The salts of C$_6$ to C$_{24}$ alkyl monoesters of polyglycoside-polycarboxylic acids may be chosen from C$_6$ to C$_{24}$ alkyl polyglycoside-citrates, C$_6$ to C$_{24}$ alkyl polyglycoside-tartrates and C$_6$ to C$_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may in particular be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Use is preferably made of alkali metal or alkaline-earth metal salts, and in particular sodium or magnesium salts.

Among the anionic surfactants mentioned, use is preferably made of (C$_6$-C$_{24}$)alkyl sulfates, (C$_6$-C$_{24}$)alkyl ether sulfates comprising from 2 to 50 ethylene oxide units, in particular in the form of alkali metal, ammonium, amino alcohol and alkaline-earth metal salts, or a mixture of these compounds.

It is in particular preferred to use (C$_{12}$-C$_{20}$)alkyl sulfates, (C$_{12}$-C$_{20}$)alkyl ether sulfates comprising from 2 to 20 ethylene oxide units, in particular in the form of alkali metal, ammonium, amino alcohol and alkaline-earth metal salts, or a mixture of these compounds. Even better still, it is preferred to use sodium lauryl ether sulfate, in particular those containing 2.2 mol of ethylene oxide, more preferentially (C$_{12}$-C$_{20}$)alkyl sulfates such as an alkali metal lauryl sulfate such as sodium lauryl sulfate.

Preferably, the anhydrous solid dyeing composition according to the present invention comprises one or more surfactants chosen from amphoteric or zwitterionic surfactants.

The amphoteric or zwitterionic surfactant(s) of the invention are preferably non-silicone, and are in particular derivatives of optionally quaternized aliphatic secondary or tertiary amines, in which derivatives the aliphatic group is a linear or branched chain comprising from 8 to 22 carbon atoms, said amine derivatives containing at least one anionic group, for instance a carboxylate, sulfonate, sulfate, phosphate or phosphonate group. Mention may be made in particular of (C$_8$-C$_{20}$)alkyl betaines, sulfobetaines, (C$_8$-C$_{20}$) alkylamido(C$_3$-C$_8$)alkyl betaines and (C$_8$-C$_{20}$)alkylamido (C$_6$-C$_8$)alkyl sulfobetaines.

Among the amphoteric or zwitterionic surfactants mentioned above, use is preferably made of (C$_8$-C$_{20}$)alkyl-betaines such as cocoylbetaine, and (C$_8$-C$_{20}$)alkylamido(C$_3$-C$_8$)alkylbetaines such as cocamidopropylbetaine, and mixtures thereof. More preferentially, the amphoteric or zwitterionic surfactant(s) are chosen from cocamidopropylbetaine and cocoylbetaine.

Preferably, the anhydrous solid dyeing composition according to the present invention comprises one or more surfactants chosen from cationic surfactants.

The cationic surfactant(s) that may be used in the composition according to the invention comprise, for example, optionally polyoxyalkylenated primary, secondary or tertiary fatty amine salts, quaternary ammonium salts, and mixtures thereof.

Among the cationic surfactants that may be present in the composition according to the invention, it is more particularly preferred to choose cetyltrimethylammonium, behenyltrimethylammonium and dipalmitoylethyl-hydroxyethyl-methylammonium salts, and mixtures thereof, and more particularly behenyltrimethylammonium chloride, cetyltrimethylammonium chloride, and dipalmitoylethylhydroxyethylammonium methosulfate, and mixtures thereof.

Preferably, the anhydrous solid dyeing composition according to the present invention comprises one or more surfactants chosen from non-ionic surfactants.

Examples of non-ionic surfactants that may be used in the composition according to the present invention are described, for example, in the "Handbook of Surfactants" by M. R. Porter, published by Blackie & Son (Glasgow and London), 1991, pp. 116-178.

Examples of non-ionic surfactants that may be mentioned include:

oxyalkylenated ($C_8$-$C_{24}$)alkylphenols;

saturated or unsaturated, linear or branched, oxyalkylenated or glycerolated $C_8$ to $C_{30}$ alcohols;

saturated or unsaturated, linear or branched, oxyalkylenated $C_8$ to $C_{30}$ amides;

esters of saturated or unsaturated, linear or branched, $C_8$ to $C_{30}$ acids and of polyethylene glycols;

polyoxyethylenated esters of saturated or unsaturated, linear or branched, $C_8$ to $C_{30}$ acids and of sorbitol;

esters of fatty acids and of sucrose;

($C_8$-$C_{30}$)alkylpolyglycosides, ($C_8$-$C_{30}$)alkenylpolyglycosides, optionally oxyalkylenated (0 to 10 oxyalkylene units) and comprising 1 to 15 glucose units, ($C_8$-$C_{30}$)alkylglucoside esters;

saturated or unsaturated oxyethylenated plant oils;

condensates of ethylene oxide and/or of propylene oxide, inter alia, alone or as mixtures;

N—($C_8$-$C_{30}$)alkylglucamine and N—($C_8$-$C_{30}$)acylmethylglucamine derivatives;

aldobionamides;

amine oxides; and oxyethylenated and/or oxypropylenated silicones.

The surfactants containing a number of moles of ethylene oxide and/or of propylene oxide ranging advantageously from 1 to 100, more particularly from 2 to 100, preferably from 2 to 50 and more advantageously from 2 to 30. Advantageously, the non-ionic surfactants do not comprise any oxypropylene units.

In accordance with a preferred embodiment of the invention, the non-ionic surfactants are chosen from oxyethylenated $C_8$ to $C_{30}$ alcohols comprising from 1 to 100 mol and more particularly from 2 to 100 mol of ethylene oxide; polyoxyethylenated esters of saturated or unsaturated, linear or branched $C_8$ to $C_{30}$ acids and of sorbitan comprising from 1 to 100 mol and better still from 2 to 100 mol of ethylene oxide.

As examples of monoglycerolated or polyglycerolated non-ionic surfactants, monoglycerolated or polyglycerolated $C_8$ to $C_{40}$ alcohols are preferably used.

In particular, the monoglycerolated or polyglycerolated $C_8$ to $C_{40}$ alcohols preferably correspond to formula (A8) below:

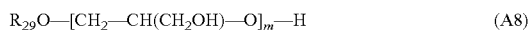

$$R_{29}O—[CH_2—CH(CH_2OH)—O]_m—H \quad (A8)$$

in which:

$R_{29}$ represents a linear or branched $C_8$ to $C_{40}$ and preferably $C_8$ to $C_{30}$ alkyl or alkenyl radical; and m represents a number ranging from 1 to 30 and preferably from 1 to 10.

As examples of compounds of formula (A8) that are suitable for use in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol comprising 2 mol of glycerol, cetearyl alcohol comprising 6 mol of glycerol, oleocetyl alcohol comprising 6 mol of glycerol and octadecanol comprising 6 mol of glycerol.

The alcohol of formula (A8) may represent a mixture of alcohols in the same way that the value of m represents a statistical value, which means that, in a commercial product, several species of polyglycerolated fatty alcohols may coexist in the form of a mixture.

Among the monoglycerolated or polyglycerolated alcohols, it is more particularly preferred to use the $C_8$ to $C_{10}$ alcohol containing 1 mol of glycerol, the $C_{10}$ to $C_{12}$ alcohol containing 1 mol of glycerol and the $C_{12}$ alcohol containing 1.5 mol of glycerol.

Preferentially, the non-ionic surfactant used in the process of the invention in the composition is a monooxyalkylenated or polyoxyalkylenated, particularly monooxyethylenated or polyoxyethylenated, or monooxypropylenated or polyoxypropylenated, non-ionic surfactant, or a combination thereof, more particularly monooxyethylenated or polyoxyethylenated, monoglycerolated or polyglycerolated surfactants and alkylpolyglucosides.

More preferably still, the non-ionic surfactants are chosen from polyoxyethylenated sorbitol esters, polyoxyethylenated fatty alcohols and alkylpolyglucosides, and mixtures thereof.

More preferentially, the anhydrous solid dyeing composition according to the present invention comprises one or more surfactants chosen from anionic surfactants, non-ionic surfactants and mixtures thereof, and more preferentially from anionic surfactants and mixtures thereof.

Alkaline Agents

The anhydrous solid dyeing composition according to the present invention may optionally also comprise one or more alkaline agents.

The alkaline agent(s) can be chosen from silicates and metasilicates such as alkali metal metasilicates, carbonates or hydrogen carbonates of alkali metals or alkaline-earth metals, such as lithium, sodium, potassium, magnesium, calcium or barium, and mixtures thereof.

The alkaline agent(s) can also be chosen from ammonium salts, and in particular inorganic ammonium salts.

Preferably, the ammonium salt(s) are chosen from ammonium halides, such as ammonium chloride, ammonium sulfate, ammonium phosphate, ammonium nitrate and mixtures thereof.

More preferentially, the ammonium salt is ammonium chloride or ammonium sulfate.

In one preferred embodiment, the anhydrous solid dyeing composition according to the present invention comprises one or more alkaline agents.

Even more preferentially, the anhydrous solid dyeing composition according to the present invention comprises one or more ammonium salts, preferably chosen from ammonium chloride or ammonium sulfate, better still ammonium sulfate.

The total amount of alkaline agent(s), when they are present in the anhydrous solid dyeing composition according to the present invention, preferably ranges from 0.1% to 50% by weight, more preferentially from 5% to 45% by weight and better still from 10% to 40% by weight, relative to the total weight of the anhydrous solid dyeing composition.

More particularly, the total amount of ammonium(s), in particular of inorganic ammonium salts, and especially ammonium sulfate, when it (they) is (are) present in the anhydrous solid dyeing composition according to the present invention, preferably ranges from 0.1% to 50% by weight, more preferentially from 5% to 45% by weight and better still from 10% to 40% by weight, relative to the total weight of the anhydrous solid dyeing composition.

Chemical Oxidizing Agents

The anhydrous solid dyeing composition according to the invention may optionally also comprise one or more chemical oxidizing agents.

According to the invention, the term "chemical oxidizing agent" is intended to mean an oxidizing agent other than atmospheric oxygen.

The anhydrous solid dyeing composition according to the present invention may comprise one or more chemical oxidizing agents, preferably one or more anhydrous chemical oxidizing agents, and more preferentially one or more anhydrous solid chemical oxidizing agents, that is to say in the form of a powder, a paste or particles (such as balls).

More particularly, the anhydrous chemical oxidizing agent(s) are chosen from (i) peroxygenated salts, for instance persulfates, perborates, peracids and precursors thereof; (ii) percarbonates of alkali metals or alkaline-earth metals, such as sodium carbonate peroxide, also known as sodium percarbonate; (iii) alkali metal bromates or ferricyanides; (iv) solid hydrogen peroxide-generating chemical oxidizing agents such as urea peroxide and polymer complexes that can release hydrogen peroxide, especially those comprising a heterocyclic vinyl monomer such as polyvinylpyrrolidone/$H_2O_2$ complexes, in particular in powder form, which are different from polymers comprising at least one heterocyclic vinyl monomer has defined below; (v) oxidases that produce hydrogen peroxide in the presence of a suitable substrate (for example glucose in the case of glucose oxidase or uric acid with uricase); (vi) mixtures thereof.

According to one particular embodiment, the chemical oxidizing agent(s) are chosen from complexes of hydrogen peroxide and of polymer containing as monomer at least one heterocyclic vinyl monomer.

More particularly, the heterocyclic vinyl monomer is chosen from monomers comprising a 4- to 6-membered heterocycle, optionally fused to a benzene ring and comprising from 1 to 4 identical or different intracyclic heteroatoms; the number of intracyclic heteroatoms being less than the number of ring members of the heterocycle. Preferably, the number of intracyclic heteroatoms is 1 or 2.

More particularly, the heteroatom(s) are chosen from sulfur, oxygen and nitrogen, preferably from nitrogen and oxygen. In accordance with an even more advantageous embodiment of the invention, the monomer comprises at least one intracyclic nitrogen atom.

The vinyl heterocycle may optionally be substituted with one or more $C_1$ to $C_4$ and preferably $C_1$ to $C_2$ alkyl groups.

Preferably, the heterocyclic monomer is chosen from N-vinyl monomers.

Among the monomers that may be envisaged, mention may be made of the following optionally substituted monomers: N-vinylpyrrolidone, vinylcaprolactam, N-vinylpiperidone, N-vinyl-3-morpholine, N-vinyl-4-oxazolinone, 2-vinylpyridine, 4-vinylpyridine, 2-vinylquinoline, 1-vinylimidazole and 1-vinylcarbazole. Preferably, the monomer is optionally substituted N-vinylpyrrolidone.

In accordance with one particularly advantageous embodiment of the invention, the polymer is a homopolymer.

However, it is not excluded to use a copolymer. In such a case, the comonomer(s) are chosen from vinyl acetate, (meth)acrylic acids, (meth)acrylamides and $C_1$ to $C_4$ alkyl esters of (meth)acrylic acid, which may be substituted or unsubstituted.

The polymer participating in this complex is preferably water-soluble. It may have variable average molecular weights, preferably between $10^3$ and $3 \times 10^6$ g/mol and more preferentially between $10^3$ and $2 \times 10^6$ g/mol. It is also possible to use mixtures of such polymers.

Advantageously, said complex comprises from 10% to 30% by weight, preferably from 13% to 25% by weight and more preferentially from 18% to 22% by weight of hydrogen peroxide relative to the total weight of the complex.

According to an even more advantageous variant of the invention, in this complex, the mole ratio between the heterocyclic vinyl monomer(s) and the hydrogen peroxide ranges from 0.5 to 2 and preferably from 0.5 to 1.

This complex is advantageously in the form of a substantially anhydrous powder.

Complexes of this type are especially described in U.S. Pat. Nos. 5,008,106, 5,077,047, EP 832 846, EP 714 919, DE 4344131 and DE 195 45 380 and the other polymer complexes described in U.S. Pat. Nos. 5,008,093, 3,376,110 and 5,183,901.

Examples of complexes that may be mentioned include products such as Peroxydone K-30, Peroxydone K-90 and Peroxydone XL-10 and also complexes formed with hydrogen peroxide and one of the following polymers such as Plasdone K-17, Plasdone K-25, Plasdone K-29/32, Plasdone K-90, Polyplasdone INF-10, Polyplasdone XL-10, Polyplasdone XL, Plasdone 5-630, Styleze 2000 Terpolymer and the series of Ganex copolymers, sold by the company ISP.

Preferably, the composition according to the present invention can comprise one or more anhydrous solid chemical oxidizing agents chosen from urea peroxide; polymer complexes that can release hydrogen peroxide, chosen from polyvinylpyrrolidone/$H_2O_2$ complexes, which are different from polymers comprising at least one heterocyclic vinyl monomer has defined below; perborates; percarbonates; and mixtures thereof.

More preferentially, the composition according to the present invention can comprise one or more anhydrous solid chemical oxidizing agents chosen from alkali metal or alkaline-earth metal percarbonates and mixtures thereof. Even better still, the chemical oxidizing agent is sodium percarbonate.

The total amount of chemical oxidizing agent(s), when they are present in the anhydrous solid dyeing composition according to the present invention, preferably ranges from 1% to 20% by weight and more preferably from 5% to 15% by weight, relative to the total weight of the composition.

According to one particularly preferred embodiment, the anhydrous solid dyeing composition according to the present invention does not comprise a chemical oxidizing agent.

Polymers Comprising at Least One Heterocyclic Vinyl Monomer

The anhydrous solid dyeing composition according to the present invention may optionally also comprise one or more polymers comprising at least one heterocyclic vinyl monomer.

More particularly, the heterocyclic vinyl monomer is chosen from monomers comprising a 4- to 7-membered heterocycle, and comprising from 1 to 4 identical or different intracyclic heteroatoms, which is optionally fused to a benzene ring and/or optionally substituted; the number of intracyclic heteroatoms being less than the number of ring members of the heterocycle.

Preferably, the number of intracyclic heteroatoms is 1 or 2.

More particularly, the heteroatom(s) are chosen from sulfur, oxygen and nitrogen, and preferably from nitrogen and oxygen.

In accordance with an even more advantageous embodiment of the invention, the monomer comprises at least one intracyclic nitrogen atom.

The vinyl heterocycle may optionally be substituted with one or more $C_1$ to $C_4$ and preferably $C_1$ to $C_2$ alkyl groups.

Preferably, the heterocyclic monomer is chosen from N-vinyl monomers.

Among the heterocyclic vinyl monomers that may be envisaged, mention may advantageously be made of the following optionally substituted monomers: N-vinylpyrrolidone, vinylcaprolactam, N-vinylpiperidone, N-vinyl-3-morpholine, N-vinyl-4-oxazolinone, 2-vinylpyridine, 4-vinylpyridine, 2-vinylquinoline, 1-vinylimidazole and 1-vinylcarbazole. Preferably, the monomer is optionally substituted N-vinylpyrrolidone.

In accordance with one particularly advantageous embodiment of the invention, the polymer is a homopolymer.

However, it is not excluded to use a copolymer. The copolymer can comprise at least two distinct heterocyclic vinyl monomers as described previously, or else at least one heterocyclic vinyl monomer, as described previously, and at least one monomer that is different from the heterocyclic vinyl monomers, as described previously.

In the latter case, the comonomer(s) are preferably chosen from vinyl acetate, (meth)acrylic acids, (meth)acrylamides and $C_1$ to $C_4$ alkyl esters of (meth)acrylic acid, which may be substituted or unsubstituted.

The polymer comprising at least one heterocyclic vinyl monomer may be crosslinked or non-crosslinked.

The polymer comprising at least one heterocyclic vinyl monomer according to the invention is preferably water-soluble. It may have variable average molecular weights, preferably between $10^3$ and $3 \times 10^6$ g/mol, and more preferentially between $10^3$ and $2 \times 10^6$ g/mol. It is also possible to use mixtures of such polymers.

Preferably, the polymer comprising at least one heterocyclic vinyl monomer is the crosslinked or non-crosslinked vinylpyrrolidone homopolymer.

The total amount of polymer(s) comprising at least one heterocyclic vinyl monomer, when they present in the anhydrous solid dyeing composition according to the present invention, preferably ranges from 5% to 70% by weight, more preferentially from 10% to 60% by weight and better still from 10% to 35% by weight, relative to the total weight of the anhydrous solid dyeing composition.

Additives

The anhydrous solid dyeing composition according to the present invention may also optionally comprise one or more additives, different from the compounds of the invention and among which mention may be made of cationic, anionic, non-ionic or amphoteric polymers or mixtures thereof, antidandruff agents, anti-seborrhoea agents, agents for preventing hair loss and/or for promoting hair regrowth, vitamins and provitamins including panthenol, sunscreens, mineral or organic pigments, sequestrants, plasticizers, solubilizers, acidifying agents, mineral or organic thickeners, in particular polymeric thickeners, opacifiers or nacreous agents, antioxidants, hydroxy acids, fragrances, preservatives, pigments and ceramides.

Needless to say, those skilled in the art will take care to select this or these optional additional compound(s) such that the advantageous properties intrinsically associated with the anhydrous solid dyeing composition in accordance with the invention are not, or are not substantially, adversely affected by the envisaged addition(s).

The above additives may generally be present in an amount, for each of them, of between 0 and 20% by weight relative to the total weight of the anhydrous solid dyeing composition.

Ready-to-Use Composition

The present invention also relates to a ready-to-use composition comprising an anhydrous solid dyeing composition, as defined above, one or more chemical oxidizing agents as defined previously, and optionally a cosmetically acceptable medium.

The term "ready-to-use composition" is intended to mean a composition intended to be applied directly to the keratin fibres without being premixed with another composition. The keratin fibres on which said ready-to-use composition is applied may be dry or wet.

The total amount of oxidation base(s) present in the ready-to-use composition according to the present invention preferably ranges from 0.05% to 15% by weight, more preferentially from 0.1% to 10% by weight, and better still from 0.5% to 5% by weight, relative to the total weight of the ready-to-use composition. The total amount of metabisulfite(s), preferably of sodium metabisulfite, present in the ready-to-use composition according to the invention preferably ranges from 0.01% to 15% by weight, more preferentially from 0.05% to 10% by weight, and better still from 0.1% to 5% by weight, relative to the total weight of the ready-to-use composition.

The total amount of coupler(s), when they are present in the ready-to-use composition according to the invention, preferably ranges from 0.05% to 15% by weight, more preferentially from 0.1% to 10% by weight, and better still from 0.5% to 5% by weight, relative to the total weight of the ready-to-use composition.

Preferably, the ready-to-use composition according to the present invention comprises one or more anhydrous solid chemical oxidizing agents chosen from urea peroxide; polymer complexes that can release hydrogen peroxide, chosen from polyvinylpyrrolidone/$H_2O_2$ complexes; perborates; percarbonates; and mixtures thereof.

More preferentially, the ready-to-use composition according to the present invention comprises one or more anhydrous solid chemical oxidizing agents chosen from percarbonates and mixtures thereof. Even better still, the chemical oxidizing agent is sodium percarbonate.

The total amount of chemical oxidizing agent(s) present in the ready-to-use composition according to the present invention preferably ranges from 0.1% to 30% by weight, more preferentially from 1% to 20% by weight, and better still from 5% to 15% by weight, relative to the total weight of the ready-to-use composition. Process for preparing the ready-to-use composition According to a first embodiment, the ready-to-use composition results from the mixing of an anhydrous solid dyeing composition as defined previously comprising one or more chemical oxidizing agents, preferably one or more anhydrous solid chemical oxidizing agents as defined previously, with a cosmetically acceptable medium.

According to a second embodiment, the ready-to-use composition results from the mixing of an anhydrous solid dyeing composition as defined previously, with one or more anhydrous solid chemical oxidizing agents as defined previously and a cosmetically acceptable medium.

According to this second embodiment, the ready-to-use composition is prepared by mixing the anhydrous solid dyeing composition and the anhydrous solid chemical oxidizing agents. Then, in a second step, a cosmetically acceptable mixture is added, in a sufficient amount, to the mixture of solid compositions previously obtained, in order to obtain the ready-to-use composition.

According to a third embodiment, the ready-to-use composition results from the mixing of an anhydrous solid dyeing composition as defined previously, with a liquid oxidizing agent comprising one or more chemical oxidizing agents.

According to this third embodiment, the ready-to-use composition is prepared by mixing the anhydrous solid dyeing composition with a sufficient amount of liquid oxidizing composition.

The term "liquid" is intended to mean a composition having a viscosity of less than or equal to 2 Pa·s, preferably less than or equal to 1 Pa·s and even better still less than or equal to 0.1 Pa·s at a temperature of 25° C., at atmospheric pressure ($1.013 \times 10^5$ Pa), and at a share rate of 1 $s^{-1}$.

In other words, when the chemical oxidizing agents are solid and anhydrous, a cosmetically acceptable medium is necessary in order to obtain the ready-to-use composition. Furthermore, when the chemical oxidizing agents are present in a liquid oxidizing composition, the cosmetically acceptable medium is not necessary in order to obtain the ready-to-use composition.

Cosmetically Acceptable Medium

The term "cosmetically acceptable medium" is intended to mean, according to the present application, a medium that is compatible with keratin fibres, in particular human keratin fibres such as the hair.

The cosmetically acceptable medium is constituted of water or of a mixture of water and of one or more organic solvents.

Examples of organic solvents that may be mentioned include linear or branched $C_2$ to $C_4$ alkanols, such as ethanol, isopropanol, tert-butanol or n-butanol; glycerol; polyols and polyol ethers, for instance 2-butoxyethanol, propylene glycol, hexylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof.

Thickening Polymers

The ready-to-use composition according to the present invention may optionally also comprise one or more thickening polymers.

Advantageously, the thickening polymer(s) are chosen from the following polymers:

(a) non-ionic amphiphilic polymers comprising at least one fatty chain and at least one hydrophilic unit;
(b) anionic amphiphilic polymers comprising at least one hydrophilic unit and at least one fatty-chain unit;
(c) crosslinked acrylic acid homopolymers;
(d) crosslinked homopolymers of 2-acrylamido-2-methylpropanesulfonic acid, and crosslinked acrylamide copolymers thereof which are partially or totally neutralized;
(e) ammonium acrylate homopolymers or copolymers of ammonium acrylate and of acrylamide;
(f) dimethylaminoethyl methacrylate homopolymers quaternized with methyl chloride or dimethylaminoethyl methacrylate copolymers quaternized with methyl chloride and acrylamide; and
(g) polysaccharides such as:
 (g1) scleroglucan gums (biopolysaccharide of microbial origin);
 (g2) gums derived from plant exudates, such as gum arabic, ghatti gum, karaya gum or gum tragacanth;
 (g3) celluloses and derivatives;
 (g4) guar gums and derivatives; or
 (g5) starches or derivatives.

It should be noted that, in the case of the present invention, the thickening polymers have a role regarding the viscosity of the ready-to-use composition.

According to the invention, amphiphilic polymers are more particularly hydrophilic polymers that are capable, in the medium of the composition, and more particularly in an aqueous medium, of reversibly combining with each other or with other molecules.

Their chemical structure more particularly comprises at least one hydrophilic group and at least one hydrophobic group. The term "hydrophobic group" is intended to mean a radical or polymer bearing a saturated or unsaturated, linear or branched hydrocarbon-based chain, comprising at least 8 carbon atoms, preferably at least 10 carbon atoms, more preferentially from 10 to 30 carbon atoms, in particular from 12 to 30 carbon atoms and even better still from 18 to 30 carbon atoms. Preferably, the hydrocarbon-based group is derived from a mono functional compound. By way of example, the hydrophobic group may be derived from a fatty alcohol such as stearyl alcohol, dodecyl alcohol or decyl alcohol. It may also denote a hydrocarbon-based polymer, such as, for example, polybutadiene.

According to a first embodiment, the thickening polymer(s) are in anhydrous solid form and are present in the anhydrous solid dyeing composition.

According to another embodiment, the thickening polymer(s) are present in the liquid oxidizing composition, as defined previously.

According to another embodiment, the thickening polymer(s) are present in the cosmetically acceptable medium.

Packaging article A subject of the present invention is also a packaging article comprising:
i) an envelope defining at least one cavity, the envelope comprising water-soluble and/or liposoluble fibres, preferably water-soluble fibres; and
ii) an anhydrous solid dyeing composition as defined previously;
it being understood that the anhydrous solid dyeing composition is in one of the cavities defined by the envelope i).

The term "water-soluble" is intended to mean soluble in water, in particular in a proportion of at least 10 grams per litre of water, preferably at least 20 g/l and better still at least 50 g/l, at a temperature of less than or equal to 35° C.

The term "liposoluble" is intended to mean soluble in a liquid fatty substance as defined below, in particular in a proportion of at least 10 grams per litre of liquid fatty substance, in particular in a plant oil or mineral oil such as liquid petroleum jelly, preferably at least 20 g/l in a liquid fatty substance, better still at least 50 g/l in a fatty substance, at a temperature of less than or equal to 35° C.

The term "temperature of less than or equal to 35° C." is intended to mean a temperature not exceeding 35° C. but greater than or equal to 0° C., for example ranging from more than 1 to 35° C., better still from 5 to 30° C. and even better still from 10 to 30° C. or 10 to 20° C. It is understood that all the temperatures are given at atmospheric pressure.

The packaging article according to the invention is preferably water-soluble or liposoluble at a temperature of less than or equal to 35° C.

The packaging article can comprise one or more cavities, at least one of which contains the anhydrous solid dyeing composition as defined previously.

According to one particular embodiment, the packaging article comprises a first cavity containing an anhydrous solid dyeing composition, as defined previously, and not comprising chemical oxidizing agent, and a second cavity containing one or more anhydrous solid chemical oxidizing agents, as defined previously.

The packaging article preferably comprises only one cavity.

According to another particular embodiment, the packaging article comprises a cavity containing an anhydrous solid dyeing composition as defined previously, said composition also comprising one or more chemical oxidizing agents, as defined previously, preferably one or more anhydrous solid chemical oxidizing agents.

The envelope may be constituted of a sheet constituted of water-soluble and/or liposoluble fibres, which is folded on itself, or of a first sheet constituted of water-soluble and/or liposoluble fibres and covered with a second sheet also constituted of water-soluble and/or liposoluble fibres. The sheet folded on itself or the two sheets are then assembled hermetically in such a way that the anhydrous solid dyeing composition according to the present invention, and optionally the anhydrous solid oxidizing agent(s), cannot diffuse to the exterior. The anhydrous solid dyeing composition, and also optionally the anhydrous solid chemical oxidizing agent(s), are thus hermetically enveloped by the envelope i). The anhydrous solid dyeing composition, and also the anhydrous solid chemical oxidizing agent(s), when they are present, are distinct from the sheet or from the envelope.

Such an envelope is different from the thin water-soluble or liposoluble films into which the anhydrous solid dyeing composition, and also optionally the anhydrous solid chemical oxidizing agent(s), would be incorporated in the sheet(s) forming the envelope. Relative to these water-soluble or liposoluble thin films, the envelope according to the invention has the advantage of allowing the incorporation of constituents that are incompatible therewith, and of being simpler to use since it does not require any premixing or any dissolution of the constituents in a solvent, or any heating to evaporate the solvent. The process for manufacturing the packaging article of the invention is also faster and less expensive than the process for manufacturing thin films.

Furthermore, when the active agents, in this case in particular the oxidation bases and the couplers, are used in dispersion to form a thin film, this may give rise to compatibility problems and mechanical problems (breaking of the film) and may impose limits on the concentration of active agents. In addition, the envelope and the sheets that are useful for the invention have the advantage of allowing wider diversity in the choice of the shape and appearance of the article, since the water-soluble and/or liposoluble sheet(s) may have a variable thickness and a variable density, giving access to a wide variety of shapes and sizes, whereas the thin film is difficult to dry if the thickness is too large, and it is fragile and difficult to manipulate if the size is too large.

Advantageously, the envelope or the sheets are "touch-deformable", which in particular means that the envelope and the sheets become deformed when they are held and pinched between a user's fingers.

Preferably, the anhydrous solid dyeing composition, and optionally the anhydrous solid chemical oxidizing agent(s), are present in a cavity generated by at least two sheets constituting the envelope and defining between them a cavity, said sheets preferably comprising water-soluble fibres.

According to a particular embodiment of the invention, at least one of the sheets of the packaging article is constituted exclusively of water-soluble fibres, and more preferentially all the sheets of the packaging article of the invention are constituted exclusively of water-soluble fibres, preferably water-soluble at a temperature of less than or equal to 30° C.

The term "fibre" is intended to mean any object of which the length is greater than its cross section. In other words, it should be understood as meaning an object of length L and of diameter D such that L is greater and preferably very much greater (i.e. at least three times greater) than D, D being the diameter of the circle in which the cross section of the fibre is inscribed. In particular, the ratio L/D (or aspect ratio) is chosen in the range from 3.5 to 2500, preferably from 5 to 500 and better still from 5 to 150. The cross section of a fibre may have any round, toothed or fluted shape, or alternatively a bean shape, but also multilobate, in particular trilobate or pentalobate, X-shaped, ribbon-shaped, square, triangular, elliptical or the like. The fibres of the invention may or may not be hollow. The fibres used according to the present invention may be of natural, synthetic or even artificial origin. Advantageously, said fibres are of synthetic origin.

A "natural fibre" is by definition a fibre that is naturally present in nature, directly or after mechanical and/or physical treatment. Fibres of animal origin, such as cellulose fibres, in particular extracted from wood, plants or algae, and rayon fibres, are collated in this category.

The "artificial fibres" are either totally synthetic or derived from natural fibres that have been subjected to one or more chemical treatments in order in particular to improve their mechanical and/or physicochemical properties.

The "synthetic fibres" collate fibres obtained by chemical synthesis and are generally fibres constituted of one or more mono-component or multi-component, composite or non-composite polymers and/or copolymers, which are generally extruded and/or drawn to the desired diameter of the fibre.

Preferably, the fibres of the invention are constituted of one or more water-soluble polymers.

The water-soluble polymer(s) of the invention contain water-soluble units in their backbones. The water-soluble units are obtained from one or more water-soluble monomers.

The term "water-soluble monomer" is intended to mean a monomer of which the solubility in water is greater than or equal to 1% and preferably greater than or equal to 5% at 25° C. and at atmospheric pressure (760 mmHg).

Said synthetic water-soluble polymer(s) used in the context of the present invention are advantageously obtained from water-soluble monomers comprising at least one double bond. These monomers may be chosen from cationic, anionic and non-ionic monomers, and mixtures thereof.

As water-soluble monomers that may be used as precursors of the water-soluble units, alone or as a mixture, examples that may be mentioned include the following monomers, which may be in free or salified form:

(meth)acrylic acid,
styrenesulfonic acid,
vinylsulfonic acid and (meth)allylsulfonic acid,
vinylphosphonic acid,
N-vinylacetamide and N-methyl-N-vinylacetamide,
N-vinylformamide and N-methyl-N-vinylformamide,
N-vinyllactams comprising a cyclic alkyl group containing from 4 to 9 carbon atoms, such as N-vinylpyrrolidone, N-butyrolactam and N-vinylcaprolactam,
maleic anhydride,
itaconic acid,
vinyl alcohol of formula $CH_2=CHOH$,
vinyl ethers of formula $CH_2=CHOR$ in which R is a linear or branched, saturated or unsaturated hydrocarbon-based radical containing from 1 to 6 carbons,
dimethyldiallylammonium halides (chloride),
quaternized dimethylaminoethyl methacrylate (DMAEMA), (meth)acrylamidopropyltrimethylammonium halides (chloride) (APTAC and MAPTAC),
methylvinylimidazolium halides (chloride),
2-vinylpyridine and 4-vinylpyridine,
acrylonitrile,
glycidyl (meth)acrylate,
vinyl halides (chloride) and vinylidene chloride,
vinyl monomers of formula (V) below:

$$H_2C=C(R)-C(O)-X \quad (V)$$

in which:
R is chosen from H and $(C_1-C_6)$alkyl such as methyl, ethyl and propyl;
X is chosen from:
alkoxy of —OR' type in which R' is a linear or branched, saturated or unsaturated hydrocarbon-based radical containing from 1 to 6 carbon atoms, optionally substituted with at least one halogen atom (iodine, bromine, chlorine or fluorine); a sulfonic ($-SO_3^-$), sulfate ($-SO_4^-$), phosphate ($-PO_4H_2$); hydroxyl (—OH); primary amine ($-NH_2$); secondary amine ($-NHR_6$), tertiary amine ($-NR_6R_7$) or quaternary amine ($-N^+R_6R_7R_8$) group with $R_6$, $R_7$ and $R_8$ being, independently of each other, a linear or branched, saturated or unsaturated hydrocarbon-based radical containing 1 to 6 carbon atoms, with the proviso that the sum of the carbon atoms of $R'+R_6+R_7+R_8$ does not exceed 6;
groups $-NH_2$, —NHR' and —NR'R" in which R' and R" are, independently of each other, linear or branched, saturated or unsaturated hydrocarbon-based radicals containing 1 to 6 carbon atoms, with the proviso that the total number of carbon atoms of R'+R" does not exceed 6, said R' and R" being optionally substituted with one halogen atom (iodine, bromine, chlorine or fluorine); a hydroxyl (—OH); sulfonic ($-SO_3^-$), sulfate ($-SO_4-$), phosphate ($-PO_4H_2$); primary amine ($-NH_2$); secondary amine ($-NHR_6$), tertiary amine ($-NR_6R_7$) and/or quaternary amine ($-N^+R_6R_7R_8$) group with $R_6$, $R_7$ and $R_8$ being, independently of each other, a linear or branched, saturated or unsaturated hydrocarbon-based radical containing 1 to 6 carbon atoms, with the proviso that the sum of the carbon atoms of $R'+R"+R_6+R_7+R_8$ does not exceed 6. As compounds corresponding to this formula, examples that may be mentioned include N,N-dimethylacrylamide and N,N-diethylacrylamide; and
mixtures thereof.
Anionic monomers that may in particular be mentioned include (meth)acrylic acid, acrylamido-2-methylpropanesulfonic acid, itaconic acid and alkali metal, alkaline-earth metal or ammonium salts thereof or salts thereof derived from an organic amine such as an alkanolamine.
Non-ionic monomers that may in particular be mentioned include (meth)acrylamide, N-vinylformamide, N-vinylacetamide, hydroxypropyl (meth)acrylate and the vinyl alcohol of formula $CH_2=CHOH$.
The cationic monomers are preferably chosen from quaternary ammonium salts derived from a diallylamine and those corresponding to formula (VI) below:

$$H_2C=C(R_1)\text{-D-N}+R_2R_3R_4,X^- \quad (VI)$$

in which:
$R_1$ represents a hydrogen atom or a methyl group,
$R_2$ and $R_3$, which may be identical or different, represent a hydrogen atom or a linear or branched $C_1$ to $C_4$ alkyl group,
$R_4$ represents a hydrogen atom or a linear or branched $C_1$ to $C_4$ alkyl group or an aryl group,
D represents the following divalent unit: $-(Y)_n-(A)-$ in which:

Y represents an amide function, an ester (O—C(O) or C(O)—O), a urethane or a urea,
A represents a linear or branched, cyclic or acyclic $C_1$ to $C_{10}$ alkylene group, which may be substituted or interrupted with a divalent aromatic or heteroaromatic group. The alkylene groups may be interrupted with an oxygen atom, a nitrogen atom, a sulfur atom or a phosphorus atom; the alkylene may be interrupted with a ketone function, an amide, an ester (O—C(O) or C(O)—O), a urethane or a urea,
n is an integer ranging from 0 to 1,
$X^-$ represents an anionic counterion, for instance a chloride or a sulfate.
Examples of water-soluble cationic monomers that may in particular be mentioned include the following compounds, and also salts thereof: dimethylaminoethyl, (meth)acryloyloxyethyltrimethylammonium, (meth)acryloyloxyethyldimethylbenzylammonium, N-[dimethylaminopropyl](meth)acrylamide, (meth)acrylamidopropyltrimethylammonium, (meth)acrylamidopropyldimethylbenzylammonium, dimethylamino hydroxypropyl, (meth)acryloyloxyhydroxypropyltrimethylammonium, (meth)acryloyloxyhydroxypropyldimethylbenzylammonium and dimethyldiallylammonium (meth)acrylate.
Preferably, the polymer of use according to the invention is polymerized from at least one cationic monomer as defined above.
Preferably, the polymers are polymerized from the following monomers comprising at least one double bond as follows:
0 to 30 mol % of acrylic acid,
0 to 95.5 mol % of acrylamide, and
0.5 mol % to 100 mol % of at least one cationic monomer represented in formula (VI) as defined above.
As polymers that are particularly preferred in the invention, mention may be made in particular of those polymerized from:
10% of acryloyloxyethyldimethylbenzylammonium chloride and 90% of acrylamide,
30% of acryloyloxytrimethylammonium chloride, 50% of acryloyloxyethyldimethylbenzylammonium chloride and 20% of acrylamide,
10% of acryloyloxyethyltrimethylammonium chloride and 90% of acrylamide,
30% of diallyldimethylammonium chloride and 70% of acrylamide, or
30% of acrylic acid and 70% of acrylamide.
According to a particular embodiment, the polymers are polymerized from a cationic monomer and acrylic acid, the number of moles of the cationic monomer being greater than the number of moles of acrylic acid.
As water-soluble polymers derived from natural products, mention may be made of polysaccharides, i.e. polymers bearing a sugar unit or sugar units.
The term "sugar unit" is intended to mean a unit resulting from a carbohydrate of formula $C_n(H_2O)_{n-1}$ or $(CH_2O)_n$, which can be optionally modified by substitution and/or by oxidation and/or by dehydration. The sugar units that may be included in the composition of the polymers of the invention are preferably derived from the following sugars: glucose, galactose, arabinose, rhamnose, mannose, xylose, fucose, fructose, anhydrogalactose, galacturonic acid, glucuronic acid, mannuronic acid, galactose sulfate or anhydrogalactose sulfate.
The polymers having a sugar unit or sugar units according to the invention can be of natural or synthetic origin. They can be non-ionic, anionic, amphoteric or cationic. The base units of the polymers having a sugar unit of the invention can be mono- or disaccharides.

Mention may in particular be made, as polymers capable of being employed, of the following native gums, and also their derivatives:

a) tree or shrub exudates, including:

gum arabic (branched polymer of galactose, arabinose, rhamnose and glucuronic acid);

ghatti gum (polymer derived from arabinose, galactose, mannose, xylose and glucuronic acid);

karaya gum (polymer derived from galacturonic acid, galactose, rhamnose and glucuronic acid);

gum tragacanth (or tragacanth) (polymer of galacturonic acid, galactose, fucose, xylose and arabinose);

b) gums resulting from algae, including:

agar (polymer derived from galactose and anhydrogalactose);

alginates (polymers of mannuronic acid and of glucuronic acid);

carrageenans and furcellerans (polymers of galactose sulfate and of anhydrogalactose sulfate);

c) gums resulting from seeds or tubers, including:

guar gum (polymer of mannose and galactose);

locust bean gum (polymer of mannose and galactose);

fenugreek gum (polymer of mannose and galactose);

tamarind gum (polymer of galactose, xylose and glucose);

konjac gum (polymer of glucose and mannose) in which the main constituent is glucomannan, a polysaccharide of high molecular weight (500 000<Mglucomannan <2 000 000) composed of D-mannose and D-glucose units with a branch every 50 or 60 units approximately;

d) microbial gums, including:

xanthan gum (polymer of glucose, mannose acetate, mannose/pyruvic acid and glucuronic acid);

gellan gum (polymer of partially acylated glucose, rhamnose and glucuronic acid);

scleroglucan gum (glucose polymer);

biosaccharide gum (polymer of galacturonic acid, fucose and D-galactose), for example the product sold under the name Fucogel 1.5P from Solabia (polysaccharide rich in fucose (20%) at 1.1% in water and stabilized (1.5% phenoxyethanol));

e) plant extracts, including:

cellulose (glucose polymer);

starch (glucose polymer);

inulin (polymer of fructose and glucose).

These polymers can be physically or chemically modified. Mention may in particular be made, as physical treatment, of the temperature. Mention may be made, as chemical treatments, of esterification, etherification, amidation or oxidation reactions. These treatments make it possible to result in polymers which can be non-ionic, anionic, cationic or amphoteric.

Preferably, these chemical or physical treatments are applied to guar gums, locust bean gums, starches and celluloses.

The non-ionic guar gums that may be used according to the invention may be modified with $C_1$ to $C_6$ hydroxyalkyl groups. Mention may be made, among the hydroxyalkyl groups, of the hydroxymethyl, hydroxyethyl, hydroxypropyl and hydroxybutyl groups.

These guar gums are well known in the prior art and may be prepared, for example, by reacting the corresponding alkene oxides, for instance, propylene oxides, with the guar gum so as to obtain a guar gum modified with hydroxypropyl groups.

The degree of hydroxyalkylation preferably varies from 0.4 to 1.2 and corresponds to the number of alkylene oxide molecules consumed by the number of free hydroxyl functional groups present on the guar gum.

Such non-ionic guar gums optionally modified with hydroxyalkyl groups are sold, for example, under the trade names Jaguar HP8, Jaguar HP60 and Jaguar HP120 by the company Rhodia Chimie.

The guar gums modified with cationic groups which can more particularly be used according to the invention are guar gums comprising trialkylammonium cationic groups. Preferably, from 2% to 30% by number of the hydroxyl functional groups of these guar gums carry trialkylammonium cationic groups. More preferably still, from 5% to 20% by number of the hydroxyl functional groups of these guar gums are branched with trialkylammonium cationic groups. Mention may very particularly be made, among these trialkylammonium groups, of the trimethylammonium and triethylammonium groups. More preferably still, these groups represent from 5% to 20% by weight, relative to the total weight of the modified guar gum.

According to the invention, use may be made of guar gums modified with 2,3-epoxypropyltrimethylammonium chloride.

These guar gums modified with cationic groups are products already known per se and are, for example, described in U.S. Pat. Nos. 3,589,578 and 4,031,307. Such products are moreover sold especially under the trade names Jaguar C13 S, Jaguar C 15 and Jaguar C 17 by the company Rhodia Chimie.

Use may be made, as modified locust bean gum, of the cationic locust bean gum containing hydroxypropyltrimonium groups, such as Catinal CLB 200 provided by Toho.

The starch molecules used in the present invention can originate from any plant starch source, in particular cereals and tubers; more particularly, they can be starches from maize, rice, cassava, barley, potato, wheat, sorghum, pea, oat or tapioca. It is also possible to use the hydrolyzates of the starches mentioned above. The starch is preferably derived from potato.

The starches can be chemically or physically modified, in particular by one or more of the following reactions: pregelatinization, oxidation, crosslinking, esterification, etherification, amidation or heat treatments.

More particularly, these reactions may be performed in the following manner:

pregelatinization by splitting the starch granules (for example drying and cooking in a drying drum);

oxidation with strong oxidizing agents, resulting in the introduction of carboxyl groups into the starch molecule and in the depolymerization of the starch molecule (for example by treating an aqueous starch solution with sodium hypochlorite);

crosslinking with functional agents capable of reacting with the hydroxyl groups of the starch molecules, which will thus be bonded together (for example with glyceryl and/or phosphate groups);

esterification in alkaline medium for the grafting of functional groups, especially $C_1$-$C_6$ acyl (acetyl), $C_1$-$C_6$ hydroxyalkyl (hydroxyethyl or hydroxypropyl), carboxymethyl or octenylsuccinic.

It is possible in particular to obtain, by crosslinking with phosphorus compounds, monostarch phosphates (of the type St-O—PO—(OX)$_2$), distarch phosphates (of the type St-O—PO—(OX)—O-St) or even tristarch phosphates (of the type St-O—PO—(O-St)$_2$) or mixtures thereof, with St meaning starch and X denoting in particular alkali metals (for example sodium or potassium), alkaline earth metals (for example calcium or magnesium), aqueous-ammonia salts, amine salts, such as those of monoethanolamine, diethanolamine, triethanolamine or 3-amino-1,2-propanediol, or ammonium salts resulting from basic amino acids, such as lysine, arginine, sarcosine, ornithine or citrulline.

The phosphorus compounds can, for example, be sodium tripolyphosphate, sodium orthophosphate, phosphorus oxychloride or sodium trimetaphosphate.

Distarch phosphates or compounds rich in distarch phosphate will preferentially be used, for instance the product sold under the references Prejel VA-70-T AGGL (gelatinized hydroxypropyl cassava distarch phosphate), Prejel TK1 (gelatinized cassava distarch phosphate) or Prejel 200 (gelatinized acetyl cassava distarch phosphate) by the company Avebe, or Structure Zea from National Starch (gelatinized corn distarch phosphate).

A preferred starch is a starch which has undergone at least one chemical modification, such as at least one esterification.

According to the invention, use may also be made of amphoteric starches comprising one or more anionic groups and one or more cationic groups. The anionic and cationic groups can be bonded to the same reactive site of the starch molecule or to different reactive sites; they are preferably bonded to the same reactive site. The anionic groups can be of carboxylic, phosphate or sulfate type, preferably of carboxylic type. The cationic groups may be of primary, secondary, tertiary or quaternary amine type.

The amphoteric starches are in particular chosen from the compounds having the following formulae:

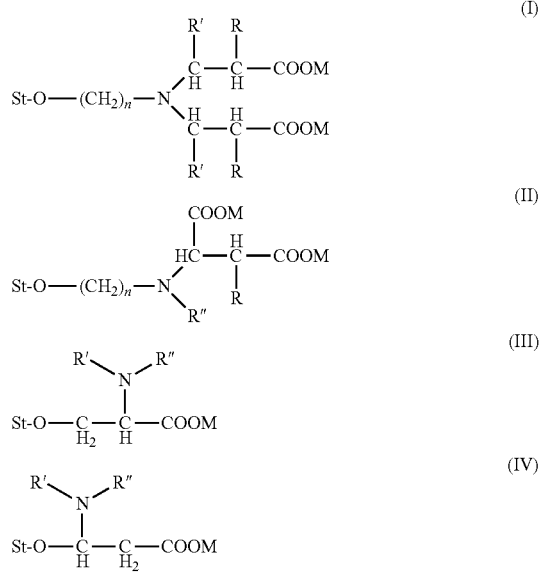

in which:
St-O represents a starch molecule;
R, which may be identical or different, represents a hydrogen atom or a methyl radical;
R', which may be identical or different, represents a hydrogen atom, a methyl radical or a group —C(O)—OH;
n is an integer equal to 2 or 3;
M, which may be identical or different, denotes a hydrogen atom, an alkali metal or alkaline-earth metal such as Na, K or Li, a quaternary ammonium $NH_4$, or an organic amine;

R" represents a hydrogen atom or a $C_1$ to $C_{18}$ alkyl radical.

These compounds are especially described in U.S. Pat. Nos. 5,455,340 and 4,017,460.

Use is in particular made of the starches of formulae (II) or (III); and preferably starches modified with 2-chloroethylaminodipropionic acid, that is to say the starches of formula (II) or (III) in which R, R', R" and M represent a hydrogen atom and n is equal to 2. The preferred amphoteric starch is a starch chloroethylamidodipropionate.

The celluloses and cellulose derivatives can be anionic, cationic, amphoteric or non-ionic.

Among these derivatives, cellulose ethers, cellulose esters and cellulose ester ethers are distinguished.

Mention may be made, among the cellulose esters, of inorganic cellulose esters (cellulose nitrates, sulfates or phosphates), organic cellulose esters (cellulose monoacetates, triacetates, amidopropionates, acetate butyrates, acetate propionates or acetate trimellitates), and mixed organic/inorganic cellulose esters, such as cellulose acetate butyrate sulfates and cellulose acetate propionate sulfates.

Mention may be made, among the cellulose ester ethers, of hydroxypropyl methylcellulose phthalates and ethylcellulose sulfates.

Mention may be made, among the non-ionic cellulose ethers, of alkylcelluloses, such as methylcelluloses and ethylcelluloses (for example Ethocel Standard 100 Premium from Dow Chemical); hydroxyalkylcelluloses, such as hydroxymethylcelluloses and hydroxyethylcelluloses (for example Natrosol 250 HHR provided by Aqualon) and hydroxypropylcelluloses (for example Klucel EF from Aqualon); and mixed hydroxyalkyl alkylcelluloses, such as hydroxypropyl methylcelluloses (for example Methocel E4M from Dow Chemical), hydroxyethyl methylcelluloses, hydroxyethyl ethylcelluloses (for example Bermocoll E 481 FQ from Akzo Nobel) and hydroxybutyl methylcelluloses.

Among the anionic cellulose ethers, mention may be made of carboxyalkyl celluloses and salts thereof. Examples that may be mentioned include carboxymethyl celluloses, carboxymethyl methyl celluloses (for example Blanose 7M from the company Aqualon) and carboxymethyl hydroxyethyl celluloses, and also the sodium salts thereof.

Among the cationic cellulose ethers, mention may be made of crosslinked or non-crosslinked quaternized hydroxyethylcelluloses. The quaternizing agent can in particular be diallyldimethylammonium chloride (for example Celquat L200 from National Starch). Mention may be made, as other cationic cellulose ether, of hydroxyethylcellulose hydroxypropyltrimethylammonium (for example Ucare polymer JR 400 from Amerchol).

Among the associative polymers bearing a sugar unit or sugar units, mention may be made of celluloses or derivatives thereof, modified with groups comprising at least one fatty chain, such as alkyl, arylalkyl or alkylaryl groups or mixtures thereof in which the alkyl groups are of $C_8$-$C_{22}$; non-ionic alkylhydroxyethylcelluloses such as the products Natrosol Plus Grade 330 CS and Polysurf 67 ($C_{16}$ alkyl) sold by the company Aqualon; quaternized alkylhydroxyethylcelluloses (cationic), such as the products Quatrisoft LM 200, Quatrisoft LM-X 529-18-A, Quatrisoft LM-X 529-18-B ($C_{12}$ alkyl) and Quatrisoft LM-X 529-8 ($C_{18}$ alkyl) sold by the company Amerchol, the products Crodacel QM and Crodacel QL ($C_{12}$ alkyl) and Crodacel QS ($C_{18}$ alkyl) sold by the company Croda, and the product Softcat SL 100 sold by the company Amerchol; non-ionic nonoxynylhydroxyethylcelluloses such as the product Amercell HM-1500 sold by the company Amerchol; non-ionic alkylcelluloses such as the product Bermocoll EHM 100 sold by the company Berol Nobel.

As associative polymers bearing a sugar unit or sugar units derived from guar, mention may be made of hydroxypropyl guars modified with a fatty chain, such as the product Esaflor HM 22 (modified with a $C_{22}$ alkyl chain) sold by the company Lamberti; the product Miracare XC 95-3 (modified with a $C_{14}$ alkyl chain) and the product RE 205-146 (modified with a $C_{20}$ alkyl chain) sold by Rhodia Chimie.

The polymer(s) having a sugar unit or sugar units of the invention are preferably chosen from guar gums, locust bean gums, xanthan gums, starches and celluloses, in their modified form (derivatives) or unmodified form.

Preferably, the polymers bearing a sugar unit or sugar units according to the invention are non-ionic.

More preferably, the polymer(s) bearing sugar units of the invention are chosen from modified non-ionic guar gums, especially modified with $C_1$ to $C_6$ hydroxyalkyl groups.

The polymers described above more particularly have a weight-average molecular weight of greater than 1 000 000 and preferably between 1 000 000 and 50 000 000. The molecular weight is determined by the RSV (Reduced Specific Viscosity) method as defined in "Principles of Polymer Chemistry" Cornell University Press, Ithaca, N.Y. 1953 Chapter VII "Determination of molecular weight" pp. 266-316.

The fibres may be spun, carded or twisted. Advantageously, the fibres used in the context of the present invention are spun. The mean diameter of the fibres used according to the present invention, which may be identical or different, is less than 500 μm. Advantageously, such a diameter is less than 200 μm, preferably less than 100 μm or even less than 50 μm.

Mention may be made more particularly of water-soluble fibres that include fibres based on polyvinyl alcohol, fibres of polysaccharides such as glucomannans, starches or celluloses such as carboxymethylcelluloses, polyalginic acid fibres, polylactic acid fibres and polyalkylene oxide fibres, and also mixtures thereof. More preferentially, the water-soluble fibre(s) used in the invention are chosen from PVA-based fibres.

The fibres of the envelope or of the sheets are generally entangled. As indicated above, the term "envelope or sheet comprising water-soluble fibres" is intended to mean an envelope or sheets which may be constituted entirely of water-soluble fibres or a sheet which may comprise both water-soluble fibres and fibres that are insoluble in water at a temperature of less than or equal to 35° C., the soluble fibres necessarily being in a larger amount than the insoluble fibres. The sheet of fibres should comprise at least 60% by weight, preferably at least 70% by weight and better still at least 80% by weight of soluble fibres relative to the total weight of fibres. It may thus comprise, for example, more than 95% by weight, or even more than 99% by weight and even 100% by weight of water-soluble fibres relative to the total weight of fibres in the envelope or the sheets.

When the sheet of fibres contains insoluble fibres, the latter fibres may be made of any material usually used as insoluble fibres; they may be, for example, silk fibre, cotton fibre, wool fibre, flax fibre, polyamide (Nylon®) fibre, polylactic acid fibre, modified cellulose (rayon, viscose or rayon acetate) fibre, poly-p-phenyleneterephthalamide fibre, in particular Kevlar® fibre, polyolefin fibre and in particular polyethylene or polypropylene fibre, glass fibre, silica fibre, aramid fibre, carbon fibre, in particular in graphite form, Teflon® fibre, insoluble collagen fibre, polyester fibre, polyvinyl or polyvinylidene chloride fibre, polyethylene terephthalate fibre, and fibres formed from a mixture of the compounds mentioned above, for instance polyamide/polyester or viscose/polyester fibres.

In addition, the envelope and the sheets of the invention may be woven or nonwoven.

According to a particular embodiment, the envelope and the sheets of the invention are woven. In the context of the present invention, a "woven" material results from an organized assembly of fibres, in particular of water-soluble polymeric fibres, and more particularly of an intercrossing, in the same plane, of said fibres, arranged in the warp direction and of fibres arranged perpendicular to the warp fibres, in the weft direction. The binding obtained between these warp and weft fibres is defined by a weave.

Such a woven material results from an operation directed towards assembling the fibres in an organized manner such as weaving per se, but may also result from knitting.

More particularly, the two layers or sheets comprising the woven polymeric water-soluble fibres that constitute the envelope of the packaging article of the invention do not comprise any other additional layer superposed thereon.

According to another particularly advantageous mode of the invention, the envelope and the sheets are nonwoven.

For the purposes of the present invention, the expression "nonwoven" is intended to mean a substrate comprising fibres, in particular water-soluble polymeric fibres, in which substrate the individual fibres are arranged in a disordered manner in a structure in the form of a sheet and which are neither woven nor knitted. The fibres of the nonwoven are generally bonded together, either under the effect of a mechanical action (for example needle punching, air jet, water jet, etc.), or under the effect of a thermal action, or by addition of a binder.

Such a nonwoven is, for example, defined by standard ISO 9092 as a web or sheet of directionally or randomly orientated fibres, bonded by friction and/or cohesion and/or adhesion, excluding paper and products obtained by weaving, knitting, tufting or stitching incorporating binding yarns or filaments.

A nonwoven differs from a paper by virtue of the length of the fibres used. In paper, the fibres are shorter. However, there are nonwovens based on cellulose fibre, which are manufactured by a wet-laid process and that have short fibres as in paper. The difference between a nonwoven and a paper is generally the absence of hydrogen bonding between the fibres in a nonwoven.

Very preferentially, the fibres used in the context of the present invention are chosen from synthetic fibres such as PVA fibres. In particular, the envelope and sheets of the invention are nonwoven, and preferentially made of nonwoven PVA fibres.

To produce the nonwoven water-soluble sheet(s) of the envelope of the packaging article, use is preferably made of PVA fibres that are soluble in water at a temperature of less than or equal to 35° C., for instance the fibres sold by the Japanese company Kuraray under the name Kuralon K-II, and particularly the grade WN2 which is soluble at and above 20° C. These fibres are described in document EP-A-636 716 which teaches the manufacture of PVA fibres that are soluble in water at temperatures not exceeding 100° C., by spinning and drawing the polyvinyl alcohol polymer in dry or wet form in the presence of solvents participating in the dissolution and solidification of the fibre. The fibre thus obtained may lead to the production of woven or nonwoven substrates. According to a particular mode of the invention, the PVA fibres of the examples of EP-A-636 716 are used, in particular Example 2 and Comparative Example 1: commercial product Solvron SS.

These fibres may also be prepared from a solution to be spun, by dissolving a water-soluble PVA-based polymer in a first organic solvent, spinning the solution in a second organic solvent to obtain solidified filaments and wet-drawing of the filaments from which the first solvent is removed, and which are then dried and subjected to a heat treatment. The cross section of these fibres may be substantially circular. These fibres have a tensile strength of at least 2.7 g/dtex (3 g/d). Patent application EP-A-0 636 716 describes such PVA-based water-soluble fibres and the process for manufacturing them. For example, the fibres may also be formed by extrusion and deposited on a conveyor to form a sheet of fibres which is then consolidated via a standard fibre bonding technique, for instance needle punching, hot-bonding, calendering or air-through bonding, in which technique the water-soluble sheet passes through a tunnel in which hot air is blown, or hydroentanglement directed towards bonding the fibres via the action of fine jets of water at very high pressure, which cannot be applied to fibres of which the dissolution temperature is too low pressure.

As has been seen previously, the invention is not limited to the use of PVA, and use may also be made of fibres made of other water-soluble materials, provided that these materials dissolve in water having the desired temperature, for example the polysaccharide fibres sold under the name Lysorb by the company Lysac Technologies, Inc. or other fibres based on polysaccharide polymers such as glucomannans or starch.

The sheets of the envelope may comprise a mixture of different fibres that are soluble in water at various temperatures (up to 35° C.).

The fibres may be composite, and they may comprise, for example, a core and a sheath not having the same nature, for example formed from different grades of PVA.

According to a particular embodiment of the invention, the sheet(s) of the envelope is (are) a nonwoven comprising water-soluble fibres, alone or as a mixture with insoluble fibres as indicated above, with not more than 40% by weight of insoluble fibres relative to the total weight of the fibres constituting the sheet. Preferably, the nonwoven is constituted essentially of water-soluble fibres, i.e. it does not contain any insoluble fibres.

The envelope may have any shape that is suitable for the intended use, for example a rectangular, circular or oval shape, and it preferably has dimensions that enable it to be held between at least two fingers. Thus, the envelope or the sheets may have, for example, an ovoid shape from about 2 to 10 cm long and from about 0.5 to 4 cm wide, or a circular disc shape from about 2 to 10 cm in diameter, or a square shape with a side length from about 5 to 15 cm, or a rectangular shape with a length from about 5 to 25 cm, it being understood that it may have any other shape and size that are suitable for the desired use.

Advantageously, the envelope and the sheets have a low thickness, the sheets possibly being constituted of several layers. Preferably, the thickness of the envelope and of the sheets ranges from 3% to 99.9% of its other dimensions. This thickness is in particular less than 100 mm. The envelope and the sheets are thus substantially flat, thin slices.

The surface delimiting the cavity(ies) has an area generally less than 625 cm$^2$, for example between 400 cm$^2$ and 0.025 cm$^2$.

Use may be made, for example, of an envelope and sheets as defined in French patent application No. FR 1 261 120 filed on 22 Nov. 2012.

The packaging article according to the present invention may comprise one or more water-soluble nonwoven sheets and envelope.

Preferentially, the amount of envelope present in the packaging article according to the invention is between 0.5% and 20% by weight relative to the total weight of said article, advantageously between 1.0% and 10.0%, particularly between 2.0% and 5.0% and more particularly 3% by weight relative to the total weight of the packaging article.

The packaging article that can contain the composition according to the invention can be illustrated by FIGS. 1a)-1e).

FIG. 1a) is a cross section of a particular embodiment of the packaging article comprising the envelope i) constituted of two sheets, which are preferably water-soluble, 11 and 12, bonded together in a peripheral region 14.

Preferably, the two sheets are joined by any suitable fixing means, preferably gluing, welding, in particular heat-welding, and in particular by entanglement.

The first sheet 11 also has a free central region D arranged facing a free central region D of the second sheet 12. These two central regions delimit a central cavity; said cavity contains an anhydrous solid dyeing composition as defined previously 13.

The sheets 11 and 12 have a closed outer perimeter 15. The shape of the outer perimeter 15 is rounded, preferably circular or elliptical, or polygonal, preferably square, rectangular or triangular, and more preferentially circular.

Figure 1B:
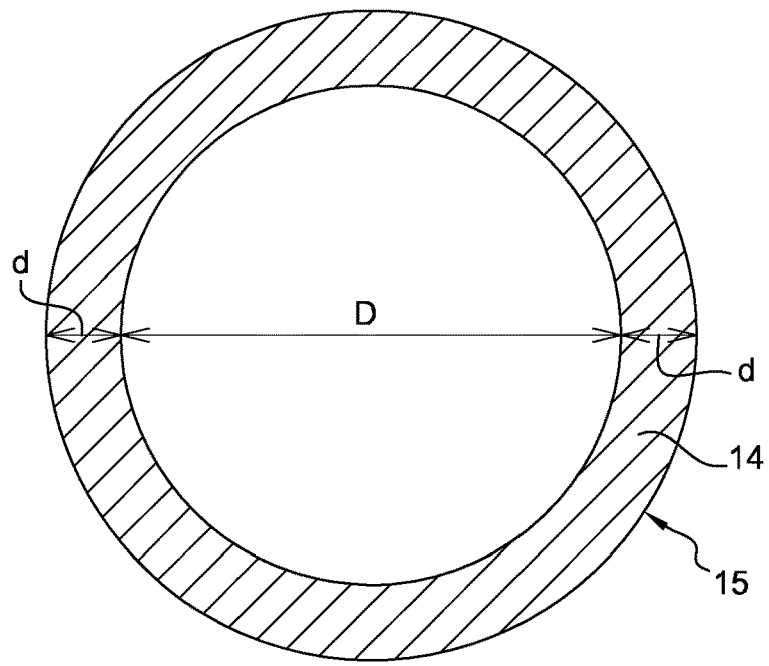
FIG. 1b) is a top view of the packaging article shown in FIG. 1a).

FIG. 1b) shows a top view of the packaging article as described in FIG. 1a), in which part D corresponds to the cavity or "central region" in which is found the anhydrous solid dyeing composition 13, and d corresponds to the peripheral region hermetically joining the two sheets 11 and 12.

Figure 1C:
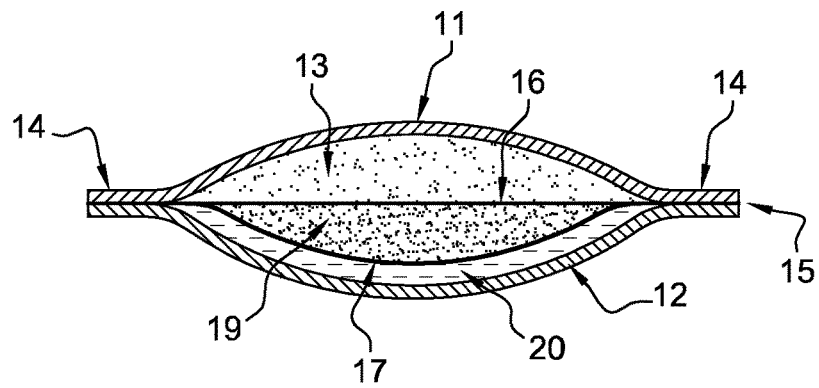
FIG. 1c) is a cross section of another embodiment of the packaging article.

FIG. 1c) shows a cross section of a particular embodiment of the packaging article, comprising an envelope constituted of two sheets 11 and 12, which are preferably water-soluble, and comprising an additional sheet 16, which is preferably water-soluble, and optionally other additional sheets 17, which are preferably water-soluble, which define several cavities in which are housed the ingredients such as the anhydrous solid dyeing composition 13 as defined previously, one or more chemical oxidizing agents, preferably anhydrous solid oxidizing agents, as defined previously, or an oxidizing composition, as defined previously, 19, and/or one or more additives 20 as defined previously.

The first sheet 11 has a thickness smaller than its other dimensions, for example less than 10% of its maximum transverse dimension D+2d.

The thickness of the first sheet 11 is, for example, less than 10 mm and in particular between 0.1 mm and 3 mm. Its maximum transverse dimension D+d is, for example, less than 100 mm, and is in particular inclusively between 10 mm and 60 mm.

The first sheet 11 thus forms a layer, for example made of nonwoven, which itself may be constituted of several layers of nonwoven that are consolidated together.

The second sheet 12 also has a closed outer perimeter 15. The outer perimeter 15 of the first sheet 11 has a shape identical to the outer perimeter 15 of the second sheet 12.

The second sheet 12 has a thickness smaller than its other dimensions, for example less than 10% of its maximum transverse dimension D+2d.

The thickness of the second sheet 12, which is preferably water-soluble, is, for example, less than 10 mm and in particular between 0.1 mm and 3 mm. Its maximum transverse dimension D+2d is less than 100 mm, and is in particular between 10 mm and 60 mm.

The thickness is advantageously measured according to the standard EDANA WSP 120.1(5).

The second sheet 12 is advantageously a nonwoven.

The first sheet 11 and the second sheet 12, which may be identical or of different thicknesses, densities and/or compositions, are preferably nonwovens that are water-soluble at a temperature of less than or equal to 35° C. The sheets and nonwoven envelope are soluble in an aqueous solution, such as water. The nonwoven sheets and envelope are preferentially made of PVA.

Figure 1D:
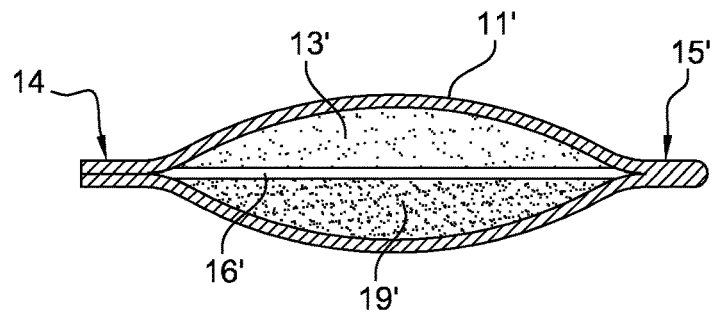
FIG. 1d) is cross section of a variant illustrating the second sheet formed by the first sheet folded on itself.
Figure 1E:
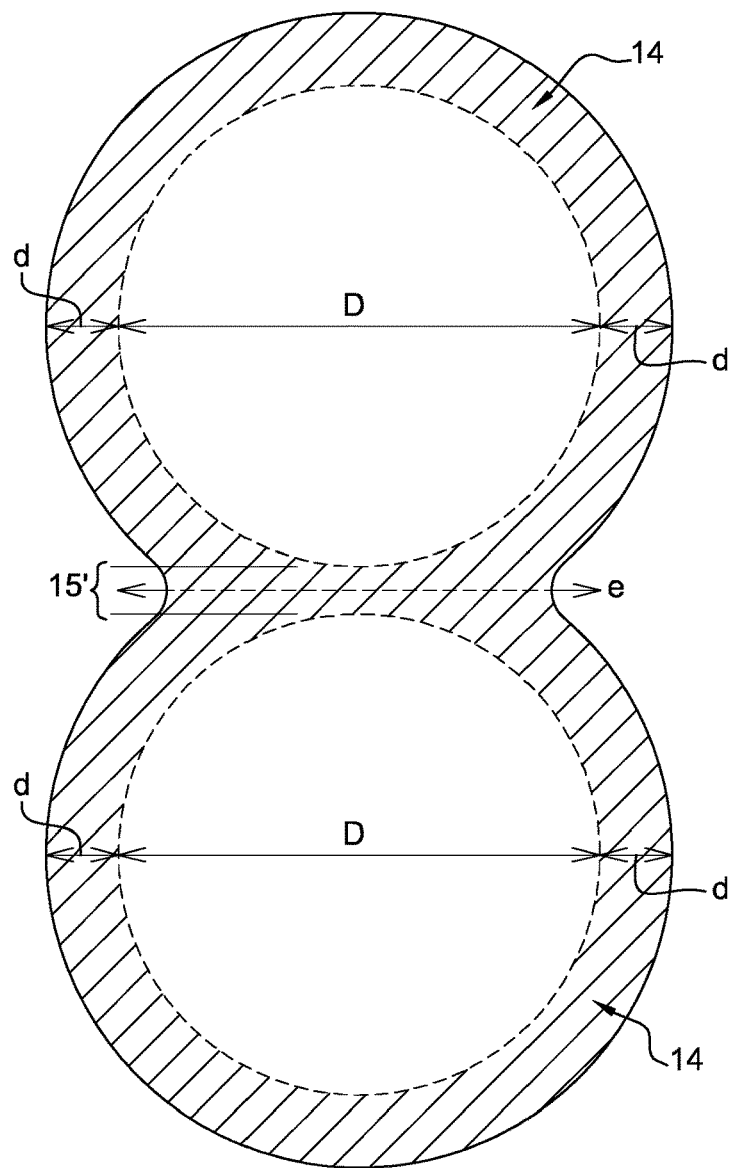
FIG. 1e) is a top view of the variant shown in FIG. 1d).

As a variant, the second sheet may be formed by the first sheet folded on itself 11' shown in FIG. 1d) in cross section and FIG. 1e) in top view. The sheet is folded on itself along the folding axis, which defines a cavity in which is the anhydrous solid dyeing composition 13' as defined previously, and optionally one or more chemical oxidizing agents, preferably anhydrous solid chemical oxidizing agents, as defined previously, or an oxidizing composition, as defined previously, 19', optionally separated by one or more water-soluble sheets 16'. The sheet 11', once filled with the ingredients 19' and with the water-soluble sheet(s) 16', is folded along the axis e, forming a folding zone 15' and then joined at a peripheral region 14, the shaded part of Figure e), preferably via any suitable fixing means such as gluing, welding, in particular heat-welding, and in particular by entanglement. The thickness of the water-soluble sheet 11' and the transverse dimensions satisfy the same criteria as those defined for the sheet 11 or 12 of FIG. 1b).

The fibres forming the first sheet 11 or 11' and the second sheet 12, and the additional sheets 16, 16' and 17, are preferably water-soluble, i.e. they are constituted of water-soluble fibres. These fibres are, for example, nonwoven water-soluble fibres such as PVA fibres, polysaccharide fibres such as glucomannans or starches, or any other polymer or compound that is capable of forming water-soluble fibres or yarns, obtained, for example, by extrusion.

The sheets 11, 11' and 12 and the optional additional sheets 16, 16' and 17, which are preferably made of nonwoven, generally have a basis weight of less than or equal to 60 g/m², or even less than or equal to 50 g/m² and better still less than or equal to 45 g/m². In one variant, the basis weight of at least one layer may be greater than 60 g/m².

The packaging articles comprising water-soluble fibres according to the invention are preferably soluble in water or in an aqueous composition with a dissolution time of the packaging article preferably of not more than one hour.

Process for Preparing the Packaging Article

The envelope i) delimits or defines a cavity that is filled with an anhydrous solid dyeing composition ii) and optionally one or more chemical oxidizing agents, preferably anhydrous solid chemical oxidizing agents, or an oxidizing composition iii). The article is then closed by folding the envelope i) on itself with its contents, followed by assembly at its periphery, for example by gluing or welding, preferably by heat-welding, or alternatively, if the article contains an envelope made up of two sheets, the anhydrous solid dyeing composition ii) and optionally one or more anhydrous solid chemical oxidizing agents or an oxidizing composition iii) are placed on the first sheet, and the article is closed by means of a second sheet which covers the ingredients ii) and iii) placed on the first sheet and which is assembled, for example, by gluing or welding at its periphery, preferably by heat-welding at its periphery, so as to obtain a hermetic article, which does not allow the powders or pastes contained in said article to pass into the atmosphere.

When the envelope and the sheets comprise several water-soluble sheets of nonwovens, these nonwovens may be assembled in particular by heat-welding at their periphery. Preferably, the heat-welding is performed with entanglement of the fibres of the parts of the envelope to be welded.

Dyeing Method

The present invention also relates to a process for dyeing keratin fibres, in particular human keratin fibres such as the hair, comprising the following successive steps:

applying to said keratin fibres a ready-to-use composition as defined previously, leaving the ready-to-use composition on said keratin fibres, rinsing said keratin fibres, and optionally shampooing said keratin fibres, rinsing them and drying them.

The present invention also relates to a process for dyeing keratin fibres, in particular human keratin fibres such as the hair, comprising the following successive steps:

mixing a packaging article, as defined previously, with a composition capable of dissolving the envelope of said packaging article, and optionally one or more chemical oxidizing agents, as defined previously, applying the resulting composition to said keratin fibres, leaving said resulting composition on said keratin fibres, rinsing said keratin fibres, and optionally shampooing said keratin fibres, rinsing them and drying them.

According to a first particular embodiment, the packaging article comprises a cavity containing an anhydrous solid dyeing composition, as defined previously, and not comprising chemical oxidizing agent. According to this embodiment, the first step of the dyeing process consists in mixing the packaging article with a composition capable of dissolving the envelope of said article, and one or more chemical oxidizing agents, as defined previously.

According to one particular embodiment, the packaging article contains a first cavity containing an anhydrous solid dyeing composition, as defined previously, and not comprising chemical oxidizing agent, and a second cavity containing one or more anhydrous solid chemical oxidizing agents, as defined previously. According to this other embodiment, the first step of the dyeing process consists in mixing the packaging article with a composition capable of dissolving the envelope of said packaging article.

According to another particular embodiment, the packaging article contains a cavity containing an anhydrous solid dyeing composition as defined previously, also comprising one or more chemical oxidizing agents, as defined previously, preferably one or more anhydrous solid chemical oxidizing agents. According to this other embodiment, the first step of the dyeing process consists in mixing the packaging article with a composition capable of dissolving the envelope of said packaging article.

It is understood that the composition capable of dissolving the envelope depends on the nature of the envelope. In other words, the composition capable of dissolving the envelope is water or an aqueous composition, when the packaging article contains predominantly or only a hydrophilic envelope. In addition, the composition capable of dissolving the envelope is an organic anhydrous composition or an aqueous composition comprising at least one liquid fatty substance or at least one organic solvent other than the liquid fatty substances, such as lower monoalcohols, for example ethanol, or such as polyols, for example propylene glycol or glycerol, when the packaging article contains predominantly or only a lipophilic envelope.

Thus, the aqueous composition may simply be water. The aqueous composition may optionally comprise at least one polar solvent. Among the polar solvents that may be used in this composition, mention may be made of organic compounds that are liquid at ambient temperature (25° C.) and at least partially water-miscible.

Examples that may be mentioned more particularly include alkanols such as ethyl alcohol, isopropyl alcohol, aromatic alcohols such as benzyl alcohol and phenylethyl alcohol, or polyols or polyol ethers, for instance ethylene glycol monomethyl, monoethyl or monobutyl ether, propylene glycol or ethers thereof, for instance propylene glycol monomethyl ether, butylene glycol, dipropylene glycol, and also diethylene glycol alkyl ethers, for instance diethylene glycol monoethyl ether or monobutyl ether.

More particularly, if one or more solvents are present, their respective content in the aqueous composition ranges from 0.5% to 20% by weight and preferably from 2% to 10% by weight relative to the weight of said aqueous composition.

The dilution ratio (expressed by weight) between one or more packaging articles, as defined previously, and the composition capable of dissolving the packaging article(s) is preferably between 10/90 and 90/10, and more preferentially between 10/90 and 50/50. Even better still, this dilution ratio is 20/80.

When the composition capable of dissolving the article is an aqueous hydrogen peroxide solution, it preferably has a pH of less than 7. The acidic pH ensures the stability of the hydrogen peroxide in the composition. It may be obtained using acidifying agents, for instance hydrochloric acid, acetic acid, etidronic acid, phosphoric acid, lactic acid or boric acid, and it may be conventionally adjusted by adding either basifying agents, for instance aqueous ammonia, monoethanolamine, diethanolamine, triethanolamine, isopropanolamine, 1,3-diaminopropane, an alkali metal or ammonium (bi)carbonate, an organic carbonate such as guanidine carbonate, or an alkali metal hydroxide, all these compounds, needless to say, possibly being taken alone or as a mixture.

The pH of the ready-to-use composition resulting from the mixing of a packaging article, as defined previously, with a composition capable of dissolving the envelope of the packaging article is preferably between 7 and 12 and more preferentially between 7.5 and 11.

In particular, the ready-to-use composition used in the dyeing process according to the invention is applied to dry or wet keratin fibres.

The ready-to-use composition is advantageously left to stand on the keratin fibres for a time ranging from 1 minute to 1 hour and more preferentially for a time ranging from 5 to 45 minutes.

The keratin fibres are then rinsed with water. They may optionally be washed with a shampoo, followed by rinsing with water, before being dried or left to dry.

The working temperature of the dyeing process according to the invention is preferably between ambient temperature (25° C.) and 80° C. and more preferentially between ambient temperature and 60° C.

Use

The present invention also relates to the use of a ready-to-use composition, as defined previously, for dyeing keratin fibres, and in particular human keratin fibres such as the hair.

A subject of the present invention is also the use of a packaging article, as defined previously, for dyeing keratin fibres, in particular human keratin fibres such as the hair.

The examples that follow serve to illustrate the invention without, however, being limiting in nature.

EXAMPLES

In the examples which follow, all the amounts are shown as percentage by weight of active material, relative to the total weight of the composition.

A. Example 1

I. Preparation of the Compositions 1.1. Dyeing Compositions

The dyeing composition (A), according to the invention, and the comparative dyeing compositions (A1) to (A7) that follow, in anhydrous powder form, were prepared from the ingredients of which the contents are indicated in the tables below (% in g of active material).

| | A invention | A1 comparative | A2 comparative | A3 comparative |
|---|---|---|---|---|
| 2,5-Toluenediamine sulfate | 29.39 | 29.39 | 29.39 | 29.39 |
| 2-methyl-5-hydroxyethylaminophenol | 22.30 | 22.30 | 22.30 | 22.30 |
| Ammonium sulfate | 30.30 | 30.30 | 30.30 | 30.30 |
| Ammonium lauryl sulfate | 6.06 | 6.06 | 6.06 | 6.06 |
| Sodium metabisulfite | 7.57 | — | — | — |
| Sodium thiosulfate | — | — | 7.57 | — |
| Cystine | — | — | — | 7.57 |
| Sorbitol | qs 100 | qs 100 | qs 100 | qs 100 |

| | A4 comparative | A5 comparative | A6 comparative | A7 comparative |
|---|---|---|---|---|
| 2,5-Toluenediamine sulfate | 29.39 | 29.39 | 29.39 | 29.39 |
| 2-methyl-5-hydroxyethylaminophenol | 22.30 | 22.30 | 22.30 | 22.30 |
| Ammonium sulfate | 30.30 | 30.30 | 30.30 | 30.30 |
| Ammonium lauryl sulfate | 6.06 | 6.06 | 6.06 | 6.06 |
| Ascorbic acid | 7.57 | — | — | — |
| Sodium sulfite | — | 7.57 | — | — |
| Cysteine | — | — | 7.57 | — |
| Glutathione | — | — | — | 7.57 |
| Sorbitol | qs 100 | qs 100 | qs 100 | qs 100 |

1.2. Oxidizing Composition

The oxidizing composition (C) was prepared from the ingredients of which the contents are indicated in the table below (% in g of active material).

| | C |
|---|---|
| Sodium percarbonate | 42.28 |
| Microcrystalline cellulose | 24.63 |
| Sorbitol | 18.38 |
| Hydroxypropyl starch phosphate | 14.71 |

II. Evaluation of the Stability of the Dyeing Compositions (Dyeing Quality)

2.1. Protocol

The dyeing quality (DQ) of each of the dyeing compositions, according to the invention (A) and comparative compositions (A1) to (A7), was evaluated. The term "dyeing quality" is intended to mean the stability over time of the colour of each of the dyeing compositions thus obtained.

The dyeing quality was measured using a Minolta CM-3600D spectrocolorimeter in the CIE L*a*b* system for each of the compositions thus obtained.

at $t_0$, that is to say just after the preparation of the composition in question, and at $t_{1\ month}$, after storage of each of these compositions for 1 month at 45° C.

The colorimetric measurements were carried out on the compositions in powder form, packaged in transparent containers.

The difference in dyeing quality (ΔDQ), that is to say the difference in colour, was then calculated for each of the dyeing compositions according to the following equation:

$$\Delta DQ = \sqrt{(L^*-L_o^*)^2+(a^*-a_o^*)^2+(b^*-b_o^*)^2}$$

The three parameters respectively denote the intensity of the colour (L*), the green/red colour axis (a*) and the blue/yellow colour axis (b*). The L*, a* and b* values are those measured on the compositions at $t_{1\ month}$ after one month of storage at 45° C. and the $L_0^*$, $a_0^*$ and $b_0^*$ values are measured on the compositions at to.

The higher the (ΔDQ) value, that is to say the higher the difference in colour, the more the dyeing composition has oxidized and the more degraded is its dyeing quality. In other words, the greater the difference, the less stable the composition is over time, and the lower the (ΔDQ) value, the more stable is the composition.

2.2. Results

The differences in dyeing quality that are obtained for each of the dyeing compositions, according to the invention (A) and comparative compositions (A1) to (A7), are indicated in the table below.

|     | A     | A1    | A2    | A3    | A4    | A5    | A6    | A7    |
| --- | ----- | ----- | ----- | ----- | ----- | ----- | ----- | ----- |
| ΔDQ | 28.11 | 46.00 | 41.10 | 46.00 | 37.47 | 47.83 | 46.76 | 36.28 |

The results obtained above show that the dyeing composition (A), prepared according to the present invention, i.e. comprising sodium metabisulfite, is more stable over time than the comparative composition (A1) not comprising sodium metabisulfite.

The composition according to the present invention is also more stable over time than the comparative compositions (A2) to (A7) comprising a reducing agent other than sodium metabisulfite.

After one month of storage at 45° C., the composition according to the invention is less oxidized than the comparative compositions, and thus retains a better dyeing quality.

III. Dyeing Evaluation of the Dyeing Compositions 3.1. Protocol

Each of the dyeing compositions (A) to (A3), (A5) and (A6), obtained previously, was mixed with the oxidizing composition (C) so as to obtain six ready-to-use compositions (A+C) to (A3+C), (A5+C) and (A6+C) comprising:

3.3 g of dyeing composition,
27.2 g of oxidizing composition (C), and
water qs 100 g.

The ready-to-use compositions thus obtained were applied to locks of hair containing 90% grey hairs, in a bath ratio equal to 5. After a leave-on time of 30 minutes at 27° C. (thermostated plate), the locks of hair were rinsed and then dried.

The same protocol was applied using dyeing compositions (A) to (A3), (A5) and (A6) previously stored for 2 months at 45° C.

The colorimetric measurements of each of the ready-to-use compositions were evaluated in the CIE L*a*b* system by means of a Minolta CM-3600D spectrocolorimeter.

In this L*a*b* system, L* represents the intensity of the colour, a* indicates the green/red colour axis and b* the blue/yellow colour axis.

The ΔE* value was calculated from the L*a*b* values according to the following equation:

$$\Delta E^* = \sqrt{(L^*-L_o^*)^2+(a^*-a_o^*)^2+(b^*-b_o^*)^2}$$

The colour build-up (ΔE*) was calculated on locks of untreated hair ($L_o^*$, $a_o^*$ and $b_o^*$) and on locks of dyed hair (L*, a* and b*). The higher the ΔE* value, the better is the build-up of the colour.

Then, the stability of the dyeing performance qualities (diffΔE), that is to say the change in the dyeing performance qualities, of the dyeing compositions (A) to (A3), (A5) and (A6) was calculated by comparing the build-up of the colouring obtained using fresh dyeing compositions, i.e. applied directly after they have been prepared, (ΔE*($t_0$)), with the build-up of the colouring obtained using dyeing compositions stored for 2 months at 45° C. (ΔE*($t_{2\ months}$)) according to the following equation:

$$\text{diff}\,\Delta E = (\Delta E^*(t_0)) - (\Delta E^*(t_{2\ months}))$$

The higher the diffΔE value, the more the dyeing performance qualities of the dyeing composition have been degraded.

3.2. Results

The diffΔE values obtained for each of the dyeing compositions, according to the invention (A) and comparative compositions (A1) to (A3), (A5) and (A6), are indicated in the table below.

|         | A   | A1   | A2  | A3  | A5  | A6  |
| ------- | --- | ---- | --- | --- | --- | --- |
| diff ΔE | 1.4 | 11.0 | 7.7 | 6.5 | 5.3 | 3.4 |

The results obtained above show that the dyeing properties of the dyeing composition (A), prepared according to the present invention, i.e. comprising sodium metabisulfite, remain more stable over time than the dyeing properties provided by the comparative composition not comprising sodium metabisulfite (A1).

The dyeing properties of the composition according to the invention are also more stable over time than those obtained with the comparative compositions (A2), (A3), (A5) and (A6) comprising a reducing agent other than sodium metabisulfite.

Even after 2 months of storage at 45° C., the composition according to the invention retains its dyeing properties, contrary to the comparative compositions.

B. Example 2

I. Preparation of the Compositions

1.1. Dyeing Compositions

The dyeing composition (B), according to the invention, and the comparative dyeing compositions (B1) to (B7) that follow, in anhydrous powder form, were prepared from the ingredients of which the contents are indicated in the tables below (% in g of active material).

|  | B invention | B1 comparative | B2 comparative | B3 comparative |
|---|---|---|---|---|
| 1-hydroxy-4-aminobenzene | 14.55 | 14.55 | 14.55 | 14.55 |
| 2,4-diaminophenoxyethanol HCl | 32.15 | 32.15 | 32.15 | 32.15 |
| Ammonium sulfate | 30.30 | 30.30 | 30.30 | 30.30 |
| Ammonium lauryl sulfate | 6.06 | 6.06 | 6.06 | 6.06 |
| Sodium metabisulfite | 7.57 | — | — | — |
| Sodium thiosulfate | — | — | 7.57 | — |
| Cystine | — | — | — | 7.57 |
| Sorbitol | qs 100 | qs 100 | qs 100 | qs 100 |

|  | B4 comparative | B5 comparative | B6 comparative | B7 comparative |
|---|---|---|---|---|
| 1-hydroxy-4-aminobenzene | 14.55 | 14.55 | 14.55 | 14.55 |
| 2,4-diaminophenoxyethanol HCl | 32.15 | 32.15 | 32.15 | 32.15 |
| Ammonium sulfate | 30.30 | 30.30 | 30.30 | 30.30 |
| Ammonium lauryl sulfate | 6.06 | 6.06 | 6.06 | 6.06 |
| Ascorbic acid | 7.57 | — | — | — |
| Sodium sulfite | — | 7.57 | — | — |
| Cysteine | — | — | 7.57 | — |
| Glutathione | — | — | — | 7.57 |
| Sorbitol | qs 100 | qs 100 | qs 100 | qs 100 |

1.2. Oxidizing Composition

The oxidizing composition (C) was prepared from the ingredients of which the contents are indicated in the table below (% in g of active material).

|  | C |
|---|---|
| Sodium percarbonate | 42.28 |
| Microcrystalline cellulose | 24.63 |
| Sorbitol | 18.38 |
| Hydroxypropyl starch phosphate | 14.71 |

II. Evaluation of the Stability of the Dyeing Compositions

2.1. Protocol

The dyeing quality (DQ) of each of the dyeing compositions, according to the invention (B) and comparative compositions (B1) to (B7), was evaluated. The term "dyeing quality" is intended to mean the stability over time of the colour of each of the dyeing compositions thus obtained.

The dyeing quality was measured using a Minolta CM-3600D spectrocolorimeter in the CIE L*a*b* system for each of the compositions thus obtained.

at $t_0$, that is to say just after the preparation of the composition in question, and at $t_{1\ month}$, after storage of each of these compositions for 1 month at 45° C.

The colorimetric measurements were carried out on the compositions in powder form, packaged in transparent containers.

The difference in dyeing quality (ΔDQ), that is to say the difference in colour, was then calculated for each of the dyeing compositions according to the following equation:

$$\Delta DQ = \sqrt{(L^*-L_o^*)^2+(a^*-a_o^*)^2+(b^*-b_o^*)^2}$$

The three parameters respectively denote the intensity of the colour (L*), the green/red colour axis (a*) and the blue/yellow colour axis (b*). The L*, a* and b* values are those measured on the compositions at $t_{1\ month}$ after one month of storage at 45° C. and the $L_o^*$, $a_o^*$ and $b_o^*$ values are measured on the compositions at to.

The higher the (ΔDQ) value, that is to say the higher the difference in colour, the more the dyeing composition has oxidized and the more degraded is its dyeing quality. In other words, the greater the difference, the less stable the composition is over time, and the lower the (ΔDQ) value, the more stable is the composition.

2.2. Results

The differences in dyeing quality that are obtained for each of the dyeing compositions, according to the invention (B) and comparative compositions (B1) to (B7), are indicated in the table below.

|  | B | B1 | B2 | B3 | B4 | B5 | B6 | B7 |
|---|---|---|---|---|---|---|---|---|
| ΔDQ | 30.22 | 47.13 | 56.57 | 56.03 | 50.39 | 51.56 | 52.35 | 56.07 |

The results obtained above show that the dyeing composition (B), prepared according to the present invention, i.e. comprising sodium metabisulfite, is more stable over time than the comparative composition (B1) not comprising sodium metabisulfite.

The composition according to the present invention is also more stable over time than the comparative compositions (B2) to (B7) comprising a reducing agent other than sodium metabisulfite.

After one month of storage at 45° C., the composition according to the invention is less oxidized than the comparative compositions, and thus retains a better dyeing quality.

III. Dyeing Evaluation of the Dyeing Compositions

3.1. Protocol

Each of the dyeing compositions (B) to (B4) and (B6), obtained previously, was mixed with the oxidizing composition (C) so as to obtain six ready-to-use compositions (B+C) to (B4+C) and (B6+C) comprising:

3.3 g of dyeing composition,
27.2 g of oxidizing composition (C), and
water qs 100 g.

The ready-to-use compositions thus obtained were then applied to locks of hair containing 90% grey hairs, in a bath ratio equal to 5. After a leave-on time of 30 minutes at 27° C. (thermostated plate), the locks of hair were rinsed and then dried.

The same protocol was applied using dyeing compositions (B) to (B6) previously stored for 2 months at 45° C.

The colorimetric measurements of each of the ready-to-use compositions were evaluated in the CIE L*a*b* system by means of a Minolta CM-3600D spectrocolorimeter.

The stability of the dyeing performance qualities (diffΔE) of the dyeing compositions (B) to (B4) and (B6) was calculated by comparing the build-up of the colouring obtained using fresh dyeing compositions, i.e. applied directly after they have been prepared, ($\Delta E^*(t_0)$), with the build-up of the colouring obtained using dyeing compositions stored for 2 months at 45° C. ($\Delta E^*(t_{2\ months})$) according to the following equation:

$$\text{diff } \Delta E = (\Delta E^*(t_0)) - (\Delta E^*(t_{2\ months}))$$

The higher the diff $\Delta E$ value, the more the dyeing performance qualities of the dyeing composition have been degraded.

3.2. Results

The $\Delta E$ values obtained for each of the dyeing compositions, according to the invention (B) and comparative compositions (B1) to (B4) and (B6), are indicated in the table below.

|  | B | B1 | B2 | B3 | B4 | B6 |
|---|---|---|---|---|---|---|
| diff $\Delta E$ | 0.36 | 10.65 | 5.34 | 4.32 | 5.21 | 15.10 |

The results obtained above show that the dyeing properties of the dyeing composition (B), prepared according to the present invention, i.e. comprising sodium metabisulfite, remain more stable over time than the dyeing properties provided by the comparative composition not comprising sodium metabisulfite (B1).

The dyeing properties of the composition according to the invention are also more stable over time than those obtained with the comparative compositions (B2) to (B4) and (B6) comprising a reducing agent other than sodium metabisulfite.

Even after 2 months of storage at 45° C., the composition according to the invention retains its dyeing properties, contrary to the comparative compositions.

The invention claimed is:

1. An anhydrous solid composition for dyeing keratin fibres comprising:
    one or more oxidation bases,
    one or more metabisulfites in a total amount ranging from 1% to 20% by weight, relative to the total weight of the anhydrous solid composition, and
    optionally one or more oxidation couplers.

2. The composition according to claim 1, characterized in that the oxidation base(s) are chosen from para-phenylenediamines, bis(phenyl)alkylenediamines, para-aminophenols, bis-para-aminophenols, ortho-aminophenols and heterocyclic bases, the addition salts thereof, the solvates thereof, and mixtures thereof.

3. The composition according to claim 2, characterized in that the oxidation base(s) are chosen from para-phenylenediamines, para-aminophenols, the addition salts thereof, the solvates thereof, and mixtures thereof.

4. The composition according to claim 1, wherein the total amount of oxidation base(s) ranges from 0.1% to 45% by weight relative to the total weight of the anhydrous solid dyeing composition.

5. The composition according to claim 1, wherein the metabisulfite(s) are chosen from alkali metal or alkaline-earth metal metabisulfites and mixtures thereof.

6. The composition according to claim 1, wherein the total amount of metabisulfite(s) ranges from 3% to 10% by weight relative to the total weight of the anhydrous solid dyeing composition.

7. The composition according to claim 1, wherein the oxidation coupler(s) are chosen from meta-phenylenediamines, meta-aminophenols, meta-diphenols, naphthalene-based couplers and heterocyclic couplers, the addition salts thereof, the solvates thereof, and mixtures thereof.

8. The composition according to claim 7, characterized in that the oxidation coupler(s) are chosen from meta-phenylenediamines, meta-aminophenols, the addition salts thereof, the solvates thereof, and mixtures thereof.

9. The composition according to claim 1, wherein the total amount of oxidation coupler(s) ranges from 0.1% to 45% by weight relative to the total weight of the anhydrous solid dyeing composition.

10. The composition according to claim 1, which also comprises one or more surfactants.

11. The composition according to claim 1, which also comprises one or more alkaline agents.

12. A packaging article comprising:
    i) an envelope defining at least one cavity, the envelope comprising water-soluble and/or liposoluble fibres; and
    ii) an anhydrous solid dyeing composition as defined according to claim 1;
    it being understood that the anhydrous solid dyeing composition is in one of the cavities defined by the envelope i).

13. The packaging article according to claim 12, characterized in that it comprises a first cavity containing the anhydrous solid dyeing composition and no chemical oxidizing agent, and a second cavity containing one or more chemical oxidizing agents.

14. The packaging article according to claim 12, characterized in that it comprises a cavity containing the anhydrous solid dyeing composition, said composition also comprising one or more chemical oxidizing agents.

15. The packaging article according to claim 12, wherein the envelope i) consists of two water-soluble or liposoluble sheets joined together at a peripheral region, the two sheets being joined by any suitable fixing means; the first sheet also has a free central region (D) arranged facing a free central region (D) of the second sheet; these two central regions defining a central cavity, said central cavity containing the anhydrous solid dyeing composition; the sheets have a closed outer periphery of which the shape is rounded.

16. The packaging article according to claim 15, which also comprises a sheet, and optionally other additional water-soluble or liposoluble sheet(s) which define one or more cavities, separating the anhydrous solid dyeing composition, one or more chemical oxidizing agents, or an oxidizing composition and/or one or more additives.

17. The packaging article according to claim 15, wherein the first sheet, the second sheet and optionally the additional sheets have a thickness smaller than their other dimensions.

18. The packaging article according to claim 15, wherein the first sheet is a nonwoven and the second sheet is a nonwoven; and said article also has a closed outer periphery; the outer periphery of the first layer is identical in shape to the outer periphery of the second layer.

19. A process for dyeing keratin fibres comprising the following successive steps:
    mixing a packaging article, as claimed in claim 12, with a composition capable of dissolving the envelope of said packaging article, and optionally one or more chemical oxidizing agents,
    applying the resulting composition to said keratin fibres,
    leaving said resulting composition on said keratin fibres,
    rinsing said keratin fibres, and
    optionally shampooing said keratin fibres, rinsing them and drying them.

20. The process as defined in claim 19 wherein the keratin fibres are human.

* * * * *